(12) United States Patent
Ito et al.

(10) Patent No.: US 9,475,796 B2
(45) Date of Patent: *Oct. 25, 2016

(54) 1-PYRAZOLYL-3-((4-((2-ANILINOPYRI-MIDIN-4-YL) OXY) NAPTHTHALEN-1-YL) UREAS AS P38 MAP KINASE INHIBITORS

(71) Applicant: RESPIVERT LIMITED, Buckinghamshire (GB)

(72) Inventors: Kazuhiro Ito, London (GB); Catherine Elisabeth Charron, London (GB); John King-Underwood, Worcestershire (GB); Stuart Thomas Onions, Nottingham (GB); Alistair Ian Longshaw, Nottingham (GB)

(73) Assignee: Respivert Limited, Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/349,356

(22) PCT Filed: Oct. 3, 2012

(86) PCT No.: PCT/GB2012/052444
§ 371 (c)(1),
(2) Date: Apr. 3, 2014

(87) PCT Pub. No.: WO2013/050756
PCT Pub. Date: Apr. 11, 2013

(65) Prior Publication Data
US 2015/0252024 A1 Sep. 10, 2015

(30) Foreign Application Priority Data

Oct. 3, 2011 (EP) .................................... 11183688

(51) Int. Cl.
C07D 403/12 (2006.01)
A61K 31/506 (2006.01)
A61K 45/06 (2006.01)
A61K 31/215 (2006.01)
A61K 31/351 (2006.01)

(52) U.S. Cl.
CPC ........... *C07D 403/12* (2013.01); *A61K 31/215* (2013.01); *A61K 31/351* (2013.01); *A61K 31/506* (2013.01); *A61K 45/06* (2013.01)

(58) Field of Classification Search
None
See application file for complete search history.

(56) References Cited

U.S. PATENT DOCUMENTS

| | | |
|---|---|---|
| 6,319,921 B1 | 11/2001 | Cirillo et al. |
| 6,492,393 B1 | 12/2002 | Breitfelder et al. |
| 6,492,529 B1 | 12/2002 | Kapadia et al. |
| 6,525,046 B1 | 2/2003 | Cirillo et al. |
| 6,583,282 B1 | 6/2003 | Zhang et al. |
| 6,852,717 B2 | 2/2005 | Cirillo et al. |
| 6,894,173 B2 | 5/2005 | Zhang et al. |
| 6,916,814 B2 | 7/2005 | Moss et al. |
| 7,041,669 B2 | 5/2006 | Cirillo et al. |
| 7,241,758 B2 | 7/2007 | Hao et al. |
| 7,329,670 B1 | 2/2008 | Dumas et al. |
| 7,384,967 B2 | 6/2008 | Polisetti et al. |
| 7,511,057 B2 | 3/2009 | Mathias |
| 7,582,638 B2 | 9/2009 | De Dios et al. |
| 7,678,811 B2 | 3/2010 | Dumas et al. |
| 7,700,620 B2 | 4/2010 | Sutton et al. |
| 7,838,524 B2 | 11/2010 | Lee et al. |
| 7,838,541 B2 | 11/2010 | Dumas et al. |
| 7,897,628 B2 | 3/2011 | Polisetti et al. |
| 8,071,616 B2 | 12/2011 | Dumas et al. |
| 8,293,748 B2 | 10/2012 | Ito et al. |
| 8,293,771 B2 | 10/2012 | Ito et al. |
| 8,299,073 B2 | 10/2012 | Ito et al. |
| 8,299,074 B2 | 10/2012 | Ito et al. |
| 8,541,424 B2 | 9/2013 | DeGoey et al. |
| 8,546,405 B2 | 10/2013 | DeGoey et al. |
| 8,618,140 B2 | 12/2013 | Ito et al. |

(Continued)

FOREIGN PATENT DOCUMENTS

WO WO 98/57937 A2 12/1998
WO WO 99/32110 A1 7/1999

(Continued)

OTHER PUBLICATIONS

U.S. Appl. No. 14/349,345, filed Apr. 2014, Ito, et al.*

(Continued)

*Primary Examiner* — Michael Barker
(74) *Attorney, Agent, or Firm* — Ada O. Wong

(57) ABSTRACT

There are provided compounds of formula (I) which are inhibitors of the family of p38 mitogen-activated protein kinase enzymes, and to their use in therapy, including in pharmaceutical combinations, especially in the treatment of inflammatory diseases, including inflammatory diseases of the lung, such as asthma and COPD.

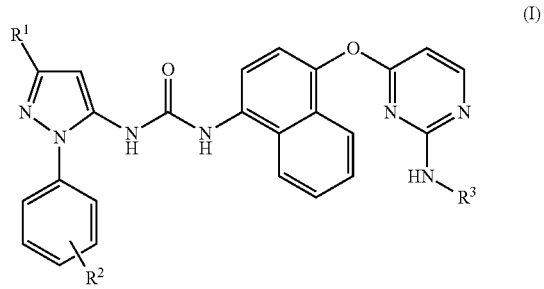

(I)

14 Claims, No Drawings

(56) References Cited

U.S. PATENT DOCUMENTS

| | | | |
|---|---|---|---|
| 8,618,289 B2 | 12/2013 | Abraham et al. |
| 8,642,773 B2 | 2/2014 | Ito et al. |
| 8,809,343 B2 | 8/2014 | Chen et al. |
| 8,927,563 B2 | 1/2015 | Fyfe et al. |
| 8,933,228 B2 | 1/2015 | Murray et al. |
| 2004/0152725 A1 | 8/2004 | Moss et al. |
| 2006/0035922 A1 | 2/2006 | Mathias et al. |
| 2007/0078121 A1 | 4/2007 | Flynn et al. |
| 2008/0300281 A1 | 12/2008 | Dumas et al. |
| 2009/0131437 A1 | 5/2009 | Furet et al. |
| 2010/0160355 A1 | 6/2010 | DeGoey et al. |
| 2010/0168138 A1 | 7/2010 | DeGoey et al. |
| 2012/0122902 A1 | 5/2012 | Chen et al. |
| 2012/0244120 A1 | 9/2012 | Charron et al. |
| 2013/0029990 A1 | 1/2013 | King-Underwood et al. |
| 2013/0040962 A1 | 2/2013 | King-Underwood et al. |
| 2013/0040995 A1 | 2/2013 | King-Underwood et al. |
| 2013/0102607 A1 | 4/2013 | Cass et al. |
| 2013/0123260 A1 | 5/2013 | Charron et al. |
| 2014/0057915 A1 | 2/2014 | Cariou et al. |
| 2014/0114061 A1 | 4/2014 | Kugimoto et al. |
| 2014/0228410 A1 | 8/2014 | Ito et al. |
| 2014/0249169 A1 | 9/2014 | Ito et al. |
| 2014/0296208 A1 | 10/2014 | Baker et al. |
| 2015/0232450 A1 | 8/2015 | Longshaw et al. |
| 2015/0329523 A1 | 11/2015 | Frickel et al. |
| 2016/0009695 A1 | 1/2016 | Ito et al. |
| 2016/0016934 A1 | 1/2016 | Fyfe |
| 2016/0039797 A1 | 2/2016 | Fyfe |
| 2016/0045482 A1 | 2/2016 | Charron |
| 2016/0096805 A1 | 4/2016 | Fyfe |
| 2016/0102059 A1 | 4/2016 | Baker et al. |
| 2016/0115152 A1 | 4/2016 | King-Underwood et al. |

FOREIGN PATENT DOCUMENTS

| | | | |
|---|---|---|---|
| WO | WO 99/32455 A1 | 7/1999 |
| WO | WO 00/43384 A1 | 7/2000 |
| WO | WO 02/092576 A1 | 11/2000 |
| WO | WO 01/04115 A2 | 1/2001 |
| WO | WO 01/36403 A1 | 5/2001 |
| WO | WO 01/64642 A2 | 9/2001 |
| WO | WO 02/083628 A1 | 10/2002 |
| WO | WO 2003/005999 A2 | 1/2003 |
| WO | WO 03/068228 A1 | 8/2003 |
| WO | WO 03/068229 A1 | 8/2003 |
| WO | WO 03/072569 A1 | 9/2003 |
| WO | WO 2004/002481 A1 | 1/2004 |
| WO | WO 2004/014387 A1 | 2/2004 |
| WO | WO 2005/110994 A1 | 11/2005 |
| WO | 2005/113556 | 12/2005 |
| WO | WO 2006/071940 A2 | 7/2006 |
| WO | WO 2006/072589 A2 | 7/2006 |
| WO | WO 2007/002635 A2 | 1/2007 |
| WO | 2007/114926 | 10/2007 |
| WO | WO 2008/067027 A2 | 6/2008 |
| WO | WO 2010/038085 A2 | 4/2010 |
| WO | WO 2010/067130 A1 | 6/2010 |
| WO | WO 2010/067131 A1 | 6/2010 |
| WO | WO 2010/075376 A2 | 7/2010 |
| WO | WO 2010/075380 A1 | 7/2010 |
| WO | WO 2010/112936 A1 | 10/2010 |
| WO | WO 2011/070368 A1 | 6/2011 |
| WO | WO 2011/070369 A1 | 6/2011 |
| WO | WO 2011/121366 A1 | 10/2011 |
| WO | WO 2011/124923 A2 | 10/2011 |
| WO | WO 2011/124930 A1 | 10/2011 |
| WO | WO 2011/153553 A2 | 12/2011 |
| WO | WO 2011/158039 A1 | 12/2011 |
| WO | WO 2011/158042 A2 | 12/2011 |
| WO | WO 2011/158044 A2 | 12/2011 |
| WO | WO 2013/050756 A1 | 4/2013 |
| WO | WO 2013/050757 A1 | 4/2013 |
| WO | WO 2014/027209 A1 | 2/2014 |
| WO | WO 2014/033446 A1 | 3/2014 |
| WO | WO 2014/033447 A1 | 3/2014 |
| WO | WO 2014/033448 A1 | 3/2014 |
| WO | WO 2014/033449 A1 | 3/2014 |
| WO | WO 2010/038086 A2 | 4/2014 |
| WO | 2014/076484 | 5/2014 |
| WO | 2014/140582 | 9/2014 |
| WO | 2014/162121 | 10/2014 |
| WO | 2015/121444 | 8/2015 |

OTHER PUBLICATIONS

O'Keefe, S.J. et al., "Chemical Genetics Define the Roles of p38α and p38β in Acute and Chronic Inflammation" *J. Biol. Chem.*, 2007, 282(48):34663-71.

Fitzsimmons, B.L. et al., "Role of spinal p38α and β MAPK in inflammatory hyperalgesia and spinal COX-2 expression", *Neuroreport*, 2010, 21(4):313-7.

Pettus et al., Small Molecule p38 MAP Kinase Inhibitors for the Treatment of Inflammatory Diseases: Novel Structures and Developments During 2006-2008 *Curr. Top. Med. Chem.*, 2008, 8(16):1452-67.

Shmueli, O. et al., "GeneNote: whole genome expression profiles in normal human tissues", *Comptes Rendus Biologies*, 2003, 326(10-11):1067-1072/Genecard.

Smith, S. et al., "Inhibitory effect of p38 mitogen-activated protein kinase inhibitors on cytokine release from human macrophages", *J. Br. I Pharmacol.*, 2006, 149:393-404.

Hale, K. K. et al., "Differential Expression and Activation of p38 Mitogen-Activated Protein Kinase α, β, γ and δ in Inflammatory Cell Lineages", *J. Immunol.*, 1999, 162(7):4246-52.

Wang, X. S. et al., "Molecular Cloning and Characterization of a Novel p38 Mitogen-activated Protein Kinase", *J. Biol. Chem.*, 1997, 272(38):23668-23674.

Court, N. W. et al., "Cardiac Expression and Subcellular Localization of the p38 Mitogen-activated Protein Kinase Member, Stress-activated Protein Kinase-3 (SAPK3)", *J. Mol. Cell. Cardiol.*, 2002, 34(4):413-26.

Mertens, S. et al., "SAP kinase-3, a new member of the family of mammalian stress-activated protein kinases", *FEBS Lett.*, 1996, 383(3):273-6.

Kuma, Y. "BIRB796 inhibits all p38 MAPK isoforms in vitro and in vivo", *J. Biol. Chem.*, 2005, 280:19472-19479.

Chung, F., "p38 Mitogen-Activated Protein Kinase Pathways in Asthma ad COPD", *Chest*, 2011, 139(6):1470-1479.

Underwood D.C. et al., "SB239063, a p38 MAPK inhibitor, reduces neutrophilia, inflammatory cytokines, MMP-9, and fibrosis in lung", *Am. J. Physiol. Lung Cell. Mol. Physiol.*, 2000, 279:895-902.

Nath, P. et al., "Importance of p38 mitogen-activated protein kinase pathway in allergic airway remodeling and bronchial hyper-responsiveness", *Eur. J. Pharmacol.*, 2006, 544:160-167.

Irusen, E. et al., "p38 Mitogen-activated protein kinase-induced glucocorticoid receptor phosphorylation reduces its activity: Role in steroid-insensitive asthma", *J. Allergy Clin. Immunol.*, 2002, 109:649-657.

Lee et al., "MAP Kinase p38 Inhibitors: Clinical Results and an Intimate Look at Their Interactions with p38α Protein", *Current Med. Chem.*, 2005, 12:2979-2994.

Mercado, N., et al., "p38 Mitogen-Activated Protein Kinase-γ Inhibition by Long-Acting β₂ Adrenergic Agonists Reversed Steroid Insensitivity in Severe Asthma", *Mol. Pharmacol.*, 2011, 80(6):1128-1135.

Papadopoulos, N.G., et al., "Mechanisms of rhinovirus-induced asthma", *Paediatr. Respir. Rev,.* 2004, 5(3):255-260.

Grunberg, K., et al., :Rhinovirus-induced Airway Inflammation in Asthma, *Am. J. Respir. Crit. Care Med.*, 2001, 164(10):1816-1822.

Wat, D., et al., "The role of respiratory viruses in cystic fibrosis", *J. Cyst. Fibros,.* 2008, 7:320-328.

Liu, M., et al., "Respiratory viral infections within one year after pediatric lung transplant", *Transpl. Infect. Dis,.* 2009, 11(4):304-312.

(56) References Cited

OTHER PUBLICATIONS

Laza-Stanca, V., et al., "Rhinovirus-induced lower respiratory illness is increased in asthma and related to virus load and Th ½ cytokine and IL-10 production", *PNAS*, 2008; 105(36):13562-13567.

Gerna, G., Piralla, A., et al., "Correlation of Phinovirus Load in the Respiratory Tract and Clinical Symptoms in Hospitalized Immunocopetent and Immunocomprised Patients", *J. Med. Virol,.* 2009, 81(8):1498-1507.

Oliver, B.G., et al., "Rhinovirus exposure impairs immune responses to bacterial products in human alveolar macrophages", *Thorax*, 2008, 63:519-525.

Wang, J.H., "Rhinovirus Enhances Various Bacterial Adhesions to Nasal Epithelial Cells Simultaneously", *The Laryngoscope*, 2009, 119(7):1406-1411.

Peleg, A.Y., et al., "Common infections in diabetes:pathogenesis, management and relationship to glycaemic control" *Diabetes Metab. Res. Rev.*, 2007, 23(1):3-13.

Kornum et al., "Diabetes, Glycemic Control, and Risk of Hospitalization with Pneumonia", *Diabetes Care*, 2008, 31(8):1541-1545.

Rollinger, J.M. et al., "The Human Rhinovirus: Human-Pathological Impact, Mechanisms of Antirhinoviral Agents, and Strategies for Their Discovery", *Med. Res. Rev.*, 2010, Doi 10.1002/med.20176.

Ludwig, S, "Influenza viruses and MAP kinase cascades-Novel targets for an antiviral intervention", 2007; *Signal Transduction*, 7:81-88.

Shin, Y.K., Liu, Q. et al., "Inlfuenza A virus NS1 protein activates the phosphatidylinositol 3-kinase (PI3K)/Akt pathway by direction interaction with the p85 subunit of PI3K", *J. Gen. Virol.*, 2007, 88:13-18.

Ehrhardt, C., Marjuki, H. et al., "Bivalent role of th ephosphatidylinostiol-3-kinase (PI3K) during influenza virus infection and host cell defence", *Cell Microbiol.*, 2006, 8:1336-1348.

Ludwig, S., et al., "MEK inhibition impairs influenza B virus propagation without emergence of resistant variants", *FEBS Lett.*, 2004, 561(1-3):37-43.

Sanderson, M.P., et al., "Syk: A Novel Target for Treatment of Inflammation in Lung Disease", *Inflamm. Allergy Drug Targets*, 2009, 8:87-95.

Lau, C. et al., "Syk Associates with Clathrin and Mediates Phosphatidylinositol 3-Kinase Activation during Human Rhinovirus Internationlaztion", *J. Immunology*, 2008, 180(2):870-880.

Bentley, J.K., et al., "Rhinovirus Activates Interleukin-8 Expression via a Src/p110β Phosphatidylinositol 3-Kinase/Akt Pthway in Human airway Epithelial Cells", *J. Virol.*, 2007, 81:1186-1194.

Inoue, D. et al, "Mechanisms of mucin production by rhinovirus infection in cultured human airway epithelial cells", *Respir. Physiol. Neurobiol.*, 2006, 154(3):484-499.

Schreiber, S. et al., "Oral p38 Mitogen-Activated Protein Kinase Inhibition with BIRB 796 for Active Crohn's Disease: A Randomized, Double Blind, Placdbo-Controlled Trial", *Clin. Gastro. Hepatology*, 2006, 4:325-334.

Shilo, Y., "ATM and Related Protein Kinases: Safeguarding Genome Integrity" *Nature Reviews Cancer*, 2003, 3:155-168.

Olaharsky, A.J. et al., "Identification of a Kinase Profile that Predicts Chromosome Damage Induced by Small Molecule Kinase Inhibitors", *PLoS Comput. Biol.*, 2009, 5(7):e1000446.

Tighe, A. et al., "GSK-3 inhibitors induce chromosome instability"; *BMC Cell Biology*, 2007, 8:34.

Pargellis, C. et al., "Inhibition of p38 MAP kinase by utilizing a novel allosteric binding site", *Nature Struct. Biol.*, 2002, 9(4):268-272.

Fabian, M.A. et al., "A small molecule-kinase interaction map for clinical kinase inhibitors", *Nature Biotechnology*, 2005, 23:329-336.

Muehlbauer P.A. et al., "Measuring the mitotic index in chemically-treated human lymphocyte cultures by flow cytomertry", *Mutation Research*, 2003, 537:117-130.

Medicherla S. et al., "p38α-Selective Mitogen-Activated Protein Kinase Inhibitor SD-282 Reduces Inflammation in a Subchronic Model of Tobacco Smoke-Induced Airway Inflammation", *J. Pharm. Exp. Ther.*, 2008, 324:921-929.

U.S. Appl. No. 14/422,158, filed Feb. 17, 2015, Cariou et al.
U.S. Appl. No. 14/424,240, filed Feb. 26, 2015, Fyfe et al.
U.S. Appl. No. 14/424,627, filed Feb. 27, 2015, Fyfe et al.
U.S. Appl. No. 14/424,361, filed Feb. 26, 2015, Duffy et al.
U.S. Appl. No. 14/424,967, filed Feb. 27, 2015, Fyfe et al.
U.S. Appl. No. 14/626,548, filed Feb. 19, 2014, Fyfe et al.
U.S. Appl. No. 14/561,290, filed Dec. 5, 2014, Murray Peter John.

Boehm et al., *New Inhibitors of p38 Kinase*, Expert Opinion in Therapeutic Patents, 10(1), pp. 25-37 (2000).

Dodeller et al., *The p38 mitogen-activated protein kinase signaling cascade in CD4 T cells*, Arthritis Research & Therapy, vol. 8, No. 2 (2006).

Douglas, Jr., *Introduction to Viral Diseases*, Cecil Textbook of Medicine, 20th Edition, W. B. Saunders Company, vol. 2, pp. 1739-1747 (1996).

Gura et al., *Systems for identifying new drugs are often faulty*, Science, 278; pp. 1041-1042 (1997).

Johnson et al., *Relationships between drug activity in NCI preclinical in vitro and in vivo models and early clinicals trials*, British Journal of Cancer, 84(10); pp. 1424-1431 (2001).

Pearce et al., *Failure modes in anticancer drug discovery and development*, Cancer Drug Design and Discovery Edited by Stephen Neidle, Chapter 18, pp. 424-435 (2008).

Simone, *Oncology:Introduction*, Cecil Textbook of Medicine, 20 Edition, W. B. Saunders Company, vol. 1 pp. 1004-1010 (1996).

Regan, et al., "Pyrazole Urea-Based Inhibitors of p38 MAP Kinase: From Lead Companies to Clinical Candidate", J. Med. Chem. 2002, 45, 2994-3008.

Moss et al., "New modifications to the area of pyrazole-naphthyl urea based 38 MAP kinase inhibitors that bind to the adenine/ATP site", Biooganic & Medicinal Chemistry Letters 2007, 17, 4242-4247.

Cirillo et al., "Discovery and characterization of the N-phenyl-N'-naphthylurea class of p38 kinase inhibitors" Bioorganic & Medicinal Chemistry Letters 2009, 19, 2386-2391.

CAS Registry No. 1379397-83-7, 2012 American Chemical Society.
CAS Registry No. 1379547-84-7, 2012 American Chemical Society.
CAS Registry No. 1379462-42-6, 2012 American Chemical Society.
CAS Registry No. 1379462-36-8, 2012 American Chemical Society.
CAS Registry No. 1379401-24-7, 2012 American Chemical Society.
CAS Registry No. 1384608-34-7, 2012 American Chemical Society.
CAS Registry No. 1384595-05-4, 2012 American Chemical Society.
CAS Registry No. 1384611-77-1, 2012 American Chemical Society.
CAS Registry No. 1384610-90-5, 2012 American Chemical Society.

Onions, et al, 2016, "The discovery of narrow spectrum kinase inhibitors: New therapeutic agents for the treatment of COPD and steroid-resistant asthma, "Journal of Medicinal Chemistry; p. 1-70.

To, et al., 2015, "Potent anti-inflammatory effects of the narrow spectrum kinase inhibitor RV1088 on rheumatoid arthritis synovial membrane cells", British Journal of Pharmacology, 172; pp. 3805-3816.

Dumas, et al., 2004, "Recent developments in the discovery of protein kinase inhibitors from the urea class", Current Opinion in Drug Discovery and Develoment 7(5): pp. 600-616.

* cited by examiner

1-PYRAZOLYL-3-((4-((2-ANILINOPYRIMIDIN-4-YL) OXY) NAPTHTHALEN-1-YL) UREAS AS P38 MAP KINASE INHIBITORS

CROSS-REFERENCE TO RELATED APPLICATIONS

This application claims the benefit of International Application Number PCT/GB2012/052444, filed 3 Oct. 2012, which claims the benefit of United Kingdom Application Number 11183688.8, filed 3 Oct. 2011. The entire contents of each of the aforesaid applications are incorporated herein by reference in their entirety.

FIELD OF THE INVENTION

The invention relates to compounds which are inhibitors of the family of p38 mitogen-activated protein kinase enzymes (referred to herein as p38 MAP kinase inhibitors), for example the alpha and gamma kinase sub-types thereof, and to their use in therapy, including in pharmaceutical combinations, especially in the treatment of inflammatory diseases, in particular inflammatory diseases of the lung, such as asthma and COPD, as well as those of the gastrointestinal tract, such as ulcerative colitis and Crohn's disease and of the eye, such as uveitis.

BACKGROUND OF THE INVENTION

Four p38 MAPK isoforms (alpha, beta, gamma and delta respectively), have been identified each displaying different patterns of tissue expression in man. The p38 MAPK alpha and beta isoforms are found ubiquitously in the body, being present in many different cell types. The alpha isoform is well characterized in terms of its role in inflammation. Although studies using a chemical genetic approach in mice indicate that the p38 MAPK beta isoform does not play a role in inflammation (O'Keefe, S. J. et al., *J. Biol. Chem.*, 2007, 282(48):34663-71.), it may be involved in pain mechanisms through the regulation of COX2 expression (Fitzsimmons, B. L. et al., *Neuroreport*, 2010, 21(4):313-7). These isoforms are inhibited by a number of previously described small molecular weight compounds. Early classes of inhibitors were highly toxic due to the broad tissue distribution of these isoforms which resulted in multiple off-target effects of the compounds. Furthermore, development of a substantial number of inhibitors has been discontinued due to unacceptable safety profiles in clinical studies (Pettus, L. H. and Wurz, R. P., *Curr. Top. Med. Chem.*, 2008, 8(16):1452-67.). As these adverse effects vary with chemotype, and the compounds have distinct kinase selectivity patterns, the observed toxicities may be structure-related rather than p38 mechanism-based.

Less is known about the p38 MAPK gamma and delta isoforms, which, unlike the alpha and beta isozymes are expressed in specific tissues and cells. The p38 MAPK-delta isoform is expressed more highly in the pancreas, testes, lung, small intestine and the kidney. It is also abundant in macrophages and detectable in neutrophils, CD4+T cells and in endothelial cells (Shmueli, O. et al., *Comptes Rendus Biologies*, 2003, 326(10-11):1067-1072; Smith, S. J. *Br. J. Pharmacol.*, 2006, 149:393-404; Hale, K. K., *J. Immunol.*, 1999, 162(7):4246-52; Wang, X. S. et al., *J. Biol. Chem.*, 1997, 272(38):23668-23674.) Very little is known about the distribution of p38 MAPK gamma although it is expressed more highly in brain, skeletal muscle and heart, as well as in lymphocytes and macrophages (Shmueli, O. et al., *Comptes Rendus Biologies*, 2003, 326(10-11):1067-1072; Hale, K. K., *J. Immunol.*, 1999, 162(7):4246-52; Court, N. W. et al., *J. Mol. Cell. Cardiol.*, 2002, 34(4):413-26; Mertens, S. et al., *FEBS Lett.*, 1996, 383(3):273-6.).

Selective small molecule inhibitors of p38 MAPK gamma and p38 MAPK delta are not currently available, although one previously disclosed compound, BIRB 796, is known to possess pan-isoform inhibitory activity. The inhibition of p38 MAPK gamma and delta isoforms is observed at higher concentrations of the compound than those required to inhibit p38 MAPK alpha and p38 beta (Kuma, Y., *J. Biol. Chem.*, 2005, 280:19472-19479.). In addition BIRB 796 also impaired the phosphorylation of p38 MAPKs or JNKs by the upstream kinase MKK6 or MKK4. Kuma discussed the possibility that the conformational change caused by the binding of the inhibitor to the MAPK protein may affect the structure of both its phosphorylation site and the docking site for the upstream activator, thereby impairing the phosphorylation of p38 MAPKs or JNKs.

p38 MAP kinase is believed to play a pivotal role in many of the signalling pathways that are involved in initiating and maintaining chronic, persistent inflammation in human disease, for example, in severe asthma and in COPD (Chung, F., *Chest*, 2011, 139(6):1470-1479.). There is now an abundant literature which demonstrates that p38 MAP kinase is activated by a range of pro-inflammatory cytokines and that its activation results in the recruitment and release of additional pro-inflammatory cytokines. Indeed, data from some clinical studies demonstrate beneficial changes in disease activity in patients during treatment with p38 MAP kinase inhibitors. For instance Smith describes the inhibitory effect of p38 MAP kinase inhibitors on TNFα (but not IL-8) release from human PBMCs.

The use of inhibitors of p38 MAP kinase in the treatment of chronic obstructive pulmonary disease (COPD) has also been proposed. Small molecule inhibitors targeted to p38 MAPK α/β have proved to be effective in reducing various parameters of inflammation in cells and in tissues obtained from patients with COPD, who are generally corticosteroid insensitive, (Smith, S. J., *Br. J. Pharmacol.*, 2006, 149:393-404.) as well as in various in vivo animal models (Underwood, D. C. et al., *Am. J. Physiol.*, 2000, 279:L895-902; Nath, P. et al., *Eur. J. Pharmacol.*, 2006, 544:160-167.). Irusen and colleagues have also suggested the possible involvement of p38 MAPK α/β with corticosteroid insensitivity via the reduction of binding affinity of the glucocorticoid receptor (GR) in nuclei (Irusen, E. et al., *J. Allergy Clin. Immunol.*, 2002, 109:649-657.). Clinical experience with a range of p38 MAP kinase inhibitors, including AMG548, BIRB 796, VX702, SCI0469 and SCI0323 has been described (Lee, M. R. and Dominguez, C., *Current Med. Chem.*, 2005, 12:2979-2994.).

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. A recent publication of Mercado (Mercado, N., et al., *Mol. Pharmacol.*, 2011, 80(6):1128-1135.) demonstrates that silencing p38 MAPK γ has the potential to restore sensitivity to corticosteroids. Consequently there may be a dual benefit for patients in the use of a p38 MAP kinase inhibitor for the treatment of COPD and severe asthma. However, the major obstacle hindering the utility of p38 MAP kinase inhibitors in the treatment of human chronic inflammatory diseases has been the severe toxicity observed in patients resulting in the withdrawal from clinical development of many compounds including all those specifically mentioned above.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

Epidemiological investigations have revealed a strong association between viral infections of the upper respiratory tract and a substantial percentage of the exacerbations suffered by patients already diagnosed with chronic respiratory diseases. Some of the most compelling data in this regard derives from longitudinal studies of children suffering from asthma (Papadopoulos, N. G., Papi, A., Psarras, S. and Johnston, S. L., *Paediatr. Respir. Rev.* 2004, 5(3):255-260.). A variety of additional studies support the conclusion that a viral infection can precipitate exacerbations and increase disease severity. For example, experimental clinical infections with rhinovirus have been reported to cause bronchial hyper-responsiveness to histamine in asthmatics that is unresponsive to treatment with corticosteroids (Grunberg, K., Sharon, R. F., et al., *Am. J. Respir. Crit. Care Med.,* 2001, 164(10):1816-1822.). Further evidence derives from the association observed between disease exacerbations in patients with cystic fibrosis and HRV infections (Wat, D., Gelder, C., et al., *J. Cyst. Fibros.* 2008, 7:320-328.). Also consistent with this body of data is the finding that respiratory viral infections, including rhinovirus, represent an independent risk factor that correlates negatively with the 12 month survival rate in paediatric, lung transplant recipients (Liu, M., Worley, S., et al., *Transpl. Infect. Dis.* 2009, 11(4):304-312.).

Clinical research indicates that the viral load is proportionate to the observed symptoms and complications and, by implication, to the severity of inflammation. For example, following experimental rhinovirus infection, lower respiratory tract symptoms and bronchial hyper-responsiveness correlated significantly with virus load (Message, S. D., Laza-Stanca, V., et al., *PNAS,* 2008; 105(36):13562-13567.). Similarly, in the absence of other viral agents, rhinovirus infections were commonly associated with lower respiratory tract infections and wheezing, when the viral load was high in immunocompetent paediatric patients (Gerna, G., Piralla, A., et al., *J. Med. Virol.* 2009, 81(8):1498-1507.).

Interestingly, it has been reported recently that prior exposure to rhinovirus reduced the cytokine responses evoked by bacterial products in human alveolar macrophages (Oliver, B. G., Lim, S., et al., *Thorax,* 2008, 63:519-525.). Additionally, infection of nasal epithelial cells with rhinovirus has been documented to promote the adhesion of bacteria, including *S. aureus* and *H. influenzae* (Wang, J. H., Kwon, H. J. and Yong, J. J., *The Laryngoscope,* 2009, 119(7):1406-1411.). Such cellular effects may contribute to the increased probability of patients suffering a lower respiratory tract infection following an infection in the upper respiratory tract. Accordingly, it is therapeutically relevant to focus on the ability of novel interventions to decrease viral load in a variety of in vitro systems, as a surrogate predictor of their benefit in a clinical setting.

High risk groups, for whom a rhinovirus infection in the upper respiratory tract can lead to severe secondary complications, are not limited to patients with chronic respiratory disease. They include, for example, the immune compromised who are prone to lower respiratory tract infection, as well as patients undergoing chemotherapy, who face acute, life-threatening fever. It has also been suggested that other chronic diseases, such as diabetes, are associated with a compromised immuno-defense response. This increases both the likelihood of acquiring a respiratory tract infection and of being hospitalised as a result (Peleg, A. Y., Weerarathna, T., et al., *Diabetes Metab. Res. Rev.,* 2007, 23(1): 3-13; Kornum, J. B., Reimar, W., et al., *Diabetes Care,* 2008, 31(8):1541-1545.).

Whilst upper respiratory tract viral infections are a cause of considerable morbidity and mortality in those patients with underlying disease or other risk factors; they also represent a significant healthcare burden in the general population and are a major cause of missed days at school and lost time in the workplace (Rollinger, J. M. and Schmidtke, M., *Med. Res. Rev.,* 2010, Doi 10.1002/med.20176.). These considerations make it clear that novel medicines, that possess improved efficacy over current therapies, are urgently required to prevent and treat rhinovirus-mediated upper respiratory tract infections. In general the strategies adopted for the discovery of improved antiviral agents have targeted various proteins produced by the virus, as the point of therapeutic intervention. However, the wide range of rhinovirus serotypes makes this a particularly challenging approach to pursue and may explain why, at the present time, a medicine for the prophylaxis and treatment of rhinovirus infections has yet to be approved by any regulatory agency.

Viral entry into the host cell is associated with the activation of a number of intracellular signalling pathways which are believed to play a prominent role in the initiation of inflammatory processes (reviewed by Ludwig, S, 2007; *Signal Transduction,* 7:81-88.) and of viral propagation and subsequent release. One such mechanism, which has been determined to play a role in influenza virus propagation in vitro, is activation of the phosphoinositide 3-kinase/Akt pathway. It has been reported that this signalling pathway is activated by the NS1 protein of the virus (Shin, Y. K., Liu, Q. et al., *J. Gen. Virol.,* 2007, 88:13-18.) and that its inhibition reduces the titres of progeny virus (Ehrhardt, C., Marjuki, H. et al., *Cell Microbiol.,* 2006, 8:1336-1348.).

Furthermore, the MEK inhibitor U0126 has been documented to inhibit viral propagation without eliciting the emergence of resistant variants of the virus (Ludwig, S., Wolff, T. et al., *FEBS Lett.,* 2004, 561(1-3):37-43.). More recently, studies targeting inhibition of Syk kinase have demonstrated that the enzyme plays an important role in mediating rhinovirus entry into cells and also virus-induced inflammatory responses, including ICAM-1 up-regulation (Sanderson, M. P., Lau, C. W. et al., *Inflamm. Allergy Drug Targets,* 2009, 8:87-95.). Syk activity is reported to be controlled by c-Src as an upstream kinase in HRV infection (Lau, C. et al., *J. Immunol.,* 2008, 180(2):870-880.). A small number of studies have appeared that link the activation of cellular Src (Src1 or p60-Src) or Src family kinases to infection with viruses. These include a report that adenovirus elicits a PI3 kinase mediated activation of Akt through a c-Src dependent mechanism. It has also been suggested that Rhinovirus-39 induced IL-8 production in epithelial cells depends upon Src kinase activation (Bentley, J. K., Newcomb, D. C., *J. Virol.*, 2007, 81:1186-1194.). Finally, it has been proposed that activation of Src kinase is involved in the induction of mucin production by rhinovirus-14 in epithelial cells and sub-mucosal glands (Inoue, D. and Yamaya, M., *Respir. Physiol. Neurobiol.*, 2006, 154(3):484-499.).

It has been disclosed previously that compounds that inhibit the activity of both c-Src and Syk kinases are effective agents against rhinovirus replication (Charron, C. E. et al., WO 2011/158042.) and that compounds that inhibit p59-HCK are effective against influenza virus replication (Charron, C. E. et al., WO 2011/070369.). For the reasons summarised above, compounds designed to treat chronic respiratory diseases that combine these inherent properties with the inhibition of p38 MAPKs, are expected to be particularly efficacious.

Certain p38 MAPK inhibitors have also been described as inhibitors of the replication of respiratory syncitial virus (Cass, L. et al., WO 2011/158039.).

Furthermore, it is noteworthy that a p38 MAPK inhibitor was found to deliver benefit for patients with IBD after one week's treatment which was not sustained over a four week course of treatment (Schreiber, S. et al., *Clin. Gastro. Hepatology*, 2006, 4:325-334.).

In addition to playing key roles in cell signalling events which control the activity of pro-inflammatory pathways, kinase enzymes are now also recognised to regulate the activity of a range of cellular functions. Among those which have been discussed recently are the maintenance of DNA integrity (Shilo, Y. *Nature Reviews Cancer*, 2003, 3:155-168.) and co-ordination of the complex processes of cell division. An illustration of recent findings is a publication describing the impact of a set of inhibitors acting upon the so-called "Olaharsky kinases" on the frequency of micronucleus formation in vitro (Olaharsky, A. J. et al., *PLoS Comput. Biol.*, 2009, 5(7):e1000446.). Micronucleus formation is implicated in, or associated with, disruption of mitotic processes and is therefore an undesirable manifestation of potential toxicity. Inhibition of glycogen synthase kinase 3α (GSK3α) was found to be a particularly significant factor that increases the likelihood of a kinase inhibitor promoting micronucleus formation. Recently, inhibition of the kinase GSK3β with RNAi was also reported to promote micronucleus formation (Tighe, A. et al., *BMC Cell Biology*, 2007, 8:34.).

It may be possible to attenuate the adverse effects arising from drug interactions with Olaharsky kinases, such as GSK3α, by optimisation of the dose and/or by changing the route of administration. However, it would be more advantageous to identify therapeutically useful molecules that demonstrate low or undetable activity against these off-target enzymes and consequently elicit little or no disruption of mitotic processes, as measured in mitosis assays.

It is evident from consideration of the literature cited hereinabove that there remains a need to identify and develop new p38 MAP kinase inhibitors that have improved therapeutic potential over currently available treatments. Desirable compounds are those that exhibit a superior therapeutic index by exerting, at the least, an equally efficacious effect as previous agents but, in one or more respects, are less toxic at the relevant therapeutic dose. An objective of the present invention therefore, is to provide such novel compounds that inhibit the enzyme activity of p38 MAP kinase, for example with certain sub-type specificities, together, preferably, with Syk kinase and tyrosine kinases within the Src family (particularly c-Src) thereby possessing good anti-inflammatory properties, and suitable for use in therapy.

In one or more embodiments of the invention disclosed herein the compounds of formula (I) exhibit a longer duration of action and/or persistence of action in comparison to the previously disclosed allosteric p38 MAP kinase inhibitor BIRB 796 (Pargellis, C. et al., *Nature Struct. Biol.*, 2002, 9(4):268-272.).

SUMMARY OF THE INVENTION

Thus in one aspect of the invention there is provided a compound of formula (I):

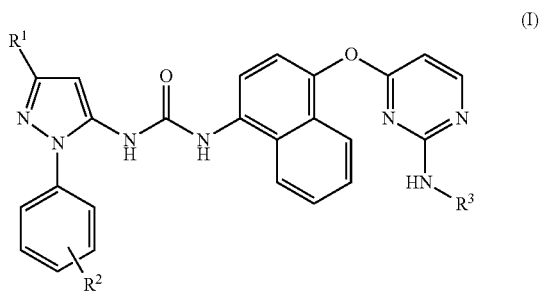

(I)

wherein:
$R^1$ represents $C_{1-10}$ alkyl, $C_{3-10}$ cycloalkyl or halo substituted $C_{1-10}$ alkyl,
$R^2$ represents hydrogen, hydroxyl, halogen, $C_{1-6}$ alkyl or $C_{1-6}$ alkoxy,
$R^3$ represents phenyl optionally substituted by 1 to 3 substituents independently selected from hydroxyl, halogen, $C_{1-6}$ alkyl and $C_{1-6}$ alkoxy,
or a pharmaceutically acceptable salt or solvate thereof, including all stereoisomers and tautomers thereof.

DETAILED DESCRIPTION OF THE INVENTION

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Alkoxy as used herein refers to straight or branched chain alkoxy, for example methoxy, ethoxy, propoxy, butoxy. Alkoxy as employed herein also extends to embodiments in which the oxygen atom is located within the alkyl chain, for example—$C_{1-3}$ alkylO$C_{1-3}$ alkyl, such as —$CH_2CH_2OCH_3$ or —$CH_2OCH_3$. Thus in one embodiment the alkoxy is linked through carbon to the remainder of the molecule. In one embodiment the alkoxy is linked through oxygen to the remainder of the molecule, for example—$OC_{1-6}$ alkyl. In one embodiment the disclosure relates to straight chain alkoxy.

Halogen includes fluoro, chloro, bromo or iodo, in particular fluoro, chloro or bromo, especially fluoro or chloro.

Alkyl substituted by halo as employed herein refers to alkyl groups having 1 to 6 halogen atoms, for example 1 to 5 halogens, such as per haloalkyl, in particular perfluoroalkyl, more specifically—$CF_2CF_3$ or $CF_3$.

$C_{1-10}$ alkyl includes $C_2$, $C_3$, $C_4$, $C_5$, $C_6$, $C_7$, $C_8$ or $C_9$ as well as $C_1$ and $C_{10}$.

In one embodiment $R^1$ is t-butyl.

In one embodiment $R^2$ represents a meta or para substituent, especially a para substituent.

In one embodiment $R^2$ represents hydrogen, methyl, methoxy or hydroxyl, for example methyl or methoxy, such as methyl.

In one embodiment $R^3$ represents unsubstituted phenyl.

In one embodiment $R^3$ represents phenyl bearing one to three substituents independently selected from methyl, ethyl, isopropyl, hydroxyl, methoxy, ethoxy, fluoro or chloro, such as independently selected from methyl, hydroxyl, methoxy or chloro.

In one embodiment the phenyl of $R^3$ bears one substituent. The selected substituent may for example be located in the 2, 3 or 4 position such as the 3 or 4 position, e.g. the 4 position.

In one embodiment the phenyl of $R^3$ bears two substituents, for example located in the 3,4 position. In another embodiment the two substituents may be located in the 2,4 position. In another embodiment the two substituents may be located in the 2,5 position.

Examples of disubstituted phenyl include 2,4-dimethoxy, 2,5-dimethyl, 2-methyl-4-chloro, 2-methyl-4-hydroxyl, 3-methoxy-4-hydroxyl, 3-hydroxyl-4-methyl, 3,4-dimethoxy, 3-chloro-4-methoxy, 3-fluoro-4-hydroxyl, 2-fluoro-4-hydroxyl, 2-chloro-4-hydroxyl and 2,4-dihydroxyl.

In one embodiment, the phenyl of $R^3$ either has hydrogen in the para position or when it bears a substituent in the para position said substituent is selected from methyl, hydroxyl, methoxy, fluoro or chloro.

Exemplary compounds of formula (I) are selected from the group consisting of:

1-(3-(tert-Butyl)-1-(p-tolyl)-1H-pyrazol-5-yl)-3-(4-(2-(phenylamino)pyrimidin-4-yloxy)naphthalen-1-yl)urea;

1-(3-(tert-Butyl)-1-(p-tolyl)-1H-pyrazol-5-yl)-3-(4-((2-((3-hydroxyphenyl)amino)pyrimidin-4-yl)oxy)naphthalen-1-yl)urea;

1-(3-(tert-butyl)-1-(4-hydroxyphenyl)-1H-pyrazol-5-yl)-3-(4-((2-(phenylamino) pyrimidin-4-yl)oxy)naphthalen-1-yl)urea;

1-(3-(tert-butyl)-1-(p-tolyl)-1H-pyrazol-5-yl)-3-(4-((2-((2-fluorophenyl)amino)pyrimidin-4-yl)oxy)naphthalen-1-yl)urea;

1-(3-(tert-butyl)-1-(p-tolyl)-1H-pyrazol-5-yl)-3-(4-((2-((2-methoxyphenyl)amino) pyrimidin-4-yl)oxy)naphthalen-1-yl)urea;

1-(3-(tert-butyl)-1-(p-tolyl)-1H-pyrazol-5-yl)-3-(4-((2-((2-chlorophenyl)amino) pyrimidin-4-yl)oxy)naphthalen-1-yl)urea;

1-(3-(tert-butyl)-1-(4-methoxyphenyl)-1H-pyrazol-5-yl)-3-(4-((2-(phenylamino) pyrimidin-4-yl)oxy)naphthalen-1-yl)urea;

1-(3-(tert-butyl)-1-(p-tolyl)-1H-pyrazol-5-yl)-3-(4-((2-((2,4-dimethoxyphenyl)amino) pyrimidin-4-yl)oxy)naphthalen-1-yl)urea;

1-(3-(tert-butyl)-1-(p-tolyl)-1H-pyrazol-5-yl)-3-(4-((2-((4-hydroxyphenyl)amino) pyrimidin-4-yl)oxy)naphthalen-1-yl)urea;

1-(3-(tert-butyl)-1-(p-tolyl)-1H-pyrazol-5-yl)-3-(4-((2-((2,5-dimethylphenyl)amino) pyrimidin-4-yl)oxy)naphthalen-1-yl)urea;

1-(3-(tert-butyl)-1-(p-tolyl)-1H-pyrazol-5-yl)-3-(4-((2-(p-tolylamino)pyrimidin-4-yl)oxy) naphthalen-1-yl)urea;

1-(3-(tert-butyl)-1-(p-tolyl)-1H-pyrazol-5-yl)-3-(4-((2-(m-tolylamino)pyrimidin-4-yl)oxy) naphthalen-1-yl)urea;

1-(3-(tert-butyl)-1-(p-tolyl)-1H-pyrazol-5-yl)-3-(4-((2-((3-chlorophenyl)amino)pyrimidin-4-yl)oxy)naphthalen-1-yl)urea;

1-(3-(tert-butyl)-1-(p-tolyl)-1H-pyrazol-5-yl)-3-(4-((2-((3-methoxyphenyl)amino) pyrimidin-4-yl)oxy)naphthalen-1-yl)urea;

1-(3-(tert-butyl)-1-(p-tolyl)-1H-pyrazol-5-yl)-3-(4-((2-((3-fluorophenyl)amino)pyrimidin-4-yl)oxy)naphthalen-1-yl)urea;

1-(3-(tert-butyl)-1-(p-tolyl)-1H-pyrazol-5-yl)-3-(4-((2-((4-chlorophenyl)amino)pyrimidin-4-yl)oxy)naphthalen-1-yl)urea;

1-(3-(tert-butyl)-1-(p-tolyl)-1H-pyrazol-5-yl)-3-(4-((2-((4-methoxyphenyl)amino) pyrimidin-4-yl)oxy)naphthalen-1-yl)urea;

1-(3-(tert-butyl)-1-(p-tolyl)-1H-pyrazol-5-yl)-3-(4-((2-((4-chloro-2-methylphenyl)amino) pyrimidin-4-yl)oxy)naphthalen-1-yl)urea;

1-(3-(tert-butyl)-1-(p-tolyl)-1H-pyrazol-5-yl)-3-(4-((2-((2-chlorophenyl)amino)pyrimidin-4-yl)oxy)naphthalen-1-yl)urea;

1-(3-(tert-butyl)-1-(p-tolyl)-1H-pyrazol-5-yl)-3-(4-((2-((2-isopropylphenyl)amino) pyrimidin-4-yl)oxy)naphthalen-1-yl)urea;

1-(3-(tert-butyl)-1-(p-tolyl)-1H-pyrazol-5-yl)-3-(4-((2-(o-tolylamino)pyrimidin-4-yl)oxy) naphthalen-1-yl)urea;

1-(3-(tert-butyl)-1-(p-tolyl)-1H-pyrazol-5-yl)-3-(4-((2-((4-ethoxyphenyl)amino)pyrimidin-4-yl)oxy)naphthalen-1-yl)urea;

1-(3-(tert-butyl)-1-(p-tolyl)-1H-pyrazol-5-yl)-3-(4-((2-((4-fluorophenyl)amino)pyrimidin-4-yl)oxy)naphthalen-1-yl)urea;

1-(3-(tert-butyl)-1-(p-tolyl)-1H-pyrazol-5-yl)-3-(4-((2-((4-hydroxy-2-methylphenyl)amino)pyrimidin-4-yl)oxy) naphthalen-1-yl)urea;

1-(3-(tert-butyl)-1-(p-tolyl)-1H-pyrazol-5-yl)-3-(4-((2-((4-hydroxy-3-methoxyphenyl)amino)pyrimidin-4-yl)oxy) naphthalen-1-yl)urea;

1-(3-(tert-butyl)-1-(p-tolyl)-1H-pyrazol-5-yl)-3-(4-((2-((3-hydroxy-4-methylphenyl)amino)pyrimidin-4-yl)oxy) naphthalen-1-yl)urea;

1-(3-(tert-butyl)-1-(p-tolyl)-1H-pyrazol-5-yl)-3-(4-((2-((3,4-dimethoxyphenyl)amino) pyrimidin-4-yl)oxy)naphthalen-1-yl)urea;

1-(3-(tert-butyl)-1-(p-tolyl)-1H-pyrazol-5-yl)-3-(4-((2-((3-chloro-4-methoxyphenyl)amino)pyrimidin-4-yl)oxy) naphthalen-1-yl)urea;

1-(3-(tert-butyl)-1-(p-tolyl)-1H-pyrazol-5-yl)-3-(4-((2-((3-fluoro-4-hydroxyphenyl)amino) pyrimidin-4-yl)oxy) naphthalen-1-yl)urea;

1-(3-(tert-butyl)-1-(p-tolyl)-1H-pyrazol-5-yl)-3-(4-((2-((2-fluoro-4-hydroxyphenyl)amino) pyrimidin-4-yl)oxy) naphthalen-1-yl)urea;

1-(3-(tert-butyl)-1-(p-tolyl)-1H-pyrazol-5-yl)-3-(4-((2-((2-chloro-4-hydroxyphenyl)amino)pyrimidin-4-yl)oxy) naphthalen-1-yl)urea;

1-(3-(tert-butyl)-1-(p-tolyl)-1H-pyrazol-5-yl)-3-(4-((2-((2,4-dihydroxyphenyl)amino) pyrimidin-4-yl)oxy)naphthalen-1-yl)urea; and 1-(3-(tert-butyl)-1-(4-methoxyphenyl)-1H-pyrazol-5-yl)-3-(4-((2-((4-hydroxyphenyl)amino)pyrimidin-4-yl)oxy) naphthalen-1-yl)urea;

and pharmaceutically acceptable salts and solvate of any one thereof, including all stereoisomers and tautomers thereof.

Examples of salts of compounds of formula (I) include all pharmaceutically acceptable salts, such as, without limitation, acid addition salts of strong mineral acids such as HCl and HBr salts and addition salts of strong organic acids such as methanesulfonic acid.

As employed herein below the definition of a compound of formula (I) is intended to include salts, solvates, and all tautomers of said compound, unless the context specifically indicates otherwise. Examples of solvates include hydrates.

The invention provided herein extends to prodrugs of the compound of formula (I), that is to say compounds which break down and/or are metabolised in vivo to provide an active compound of formula (I). General examples of prodrugs include simple esters, and other esters such as mixed carbonate esters, carbamates, glycosides, ethers, acetals and ketals.

In a further aspect of the invention there is provided one or more metabolites of the compound of formula (I), in particular a metabolite that retains one or more of the therapeutic activities of the compound of formula (I). A metabolite, as employed herein, is a compound that is produced in vivo from the metabolism of the compound of formula (I), such as, without limitation, oxidative metabolites and/or metabolites generated, for example, from 0-dealkylation.

The compounds of the disclosure include those where the atom specified is a naturally occurring or non-naturally occurring isotope. In one embodiment the isotope is a stable isotope. Thus the compounds of the disclosure include, for example deuterium containing compounds and the like.

The disclosure also extends to all polymorphic forms of the compounds herein defined.

Two generic routes by which compound examples of the invention may be conveniently prepared are summarised below (Scheme 1).

Thus compounds of formula (I) may be obtained by a general process, Route A, whereby a naphthylamine precursor represented by Intermediate B is coupled with an activated, electrophilic derivative represented by Intermediate A* prepared from the corresponding amine precursor Intermediate A (X=H). The fragment $LG_1$ in Intermediate A* is a suitable leaving group such as an imidazoyl ($C_3H_3N_2$) or a phenoxy ($C_6H_5O$) radical.

In the first case the electrophilic compounds, Intermediate A* are obtained by reaction of the corresponding amine with CDI in a non polar aprotic solvent, such as DCM and are conveniently generated in situ at RT and then reacted without isolation with compounds represented by Intermediate B. In the second case the required activated amine components may be generated by treatment of the amine precursors with a suitable chloroformate, such as, for example, phenyl chloroformate, in the presence of a base. The activation process is conveniently carried out under Schotten Baumann type conditions, that is using an aqueous base, such as aq sodium carbonate and under biphasic conditions. The activated amine derivatives represented by Intermediate A, wherein LG, is a aryloxy, for example phenoxy, may also be generated optionally in situ and then reacted without isolation with compounds represented by Intermediate B to provide compound examples of formula (I).

In addition, compounds of the invention may be generated by an alternative synthetic process Route B, employing a displacement reaction between an appropriate amine ($R^3NH_2$) and a pyrimidine compound represented by Intermediate C in which $LG_2$ is a suitable leaving group such as a halogen, for example, a chlorine atom. The reaction proceeds under acidic conditions, in a suitable organic solvent for example in the presence of p-TSA and in THF.

Scheme 1

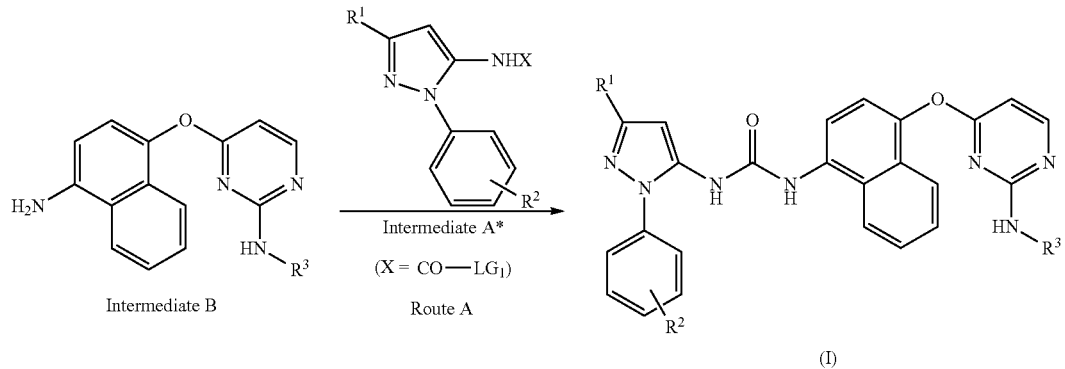

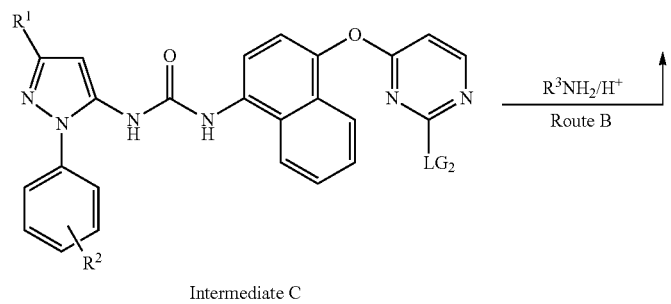

Intermediate C

Compounds represented by Intermediate B and Intermediate C may be obtained using the same two transformative processes described herein above starting from compounds represented by Intermediate D (Scheme 2).

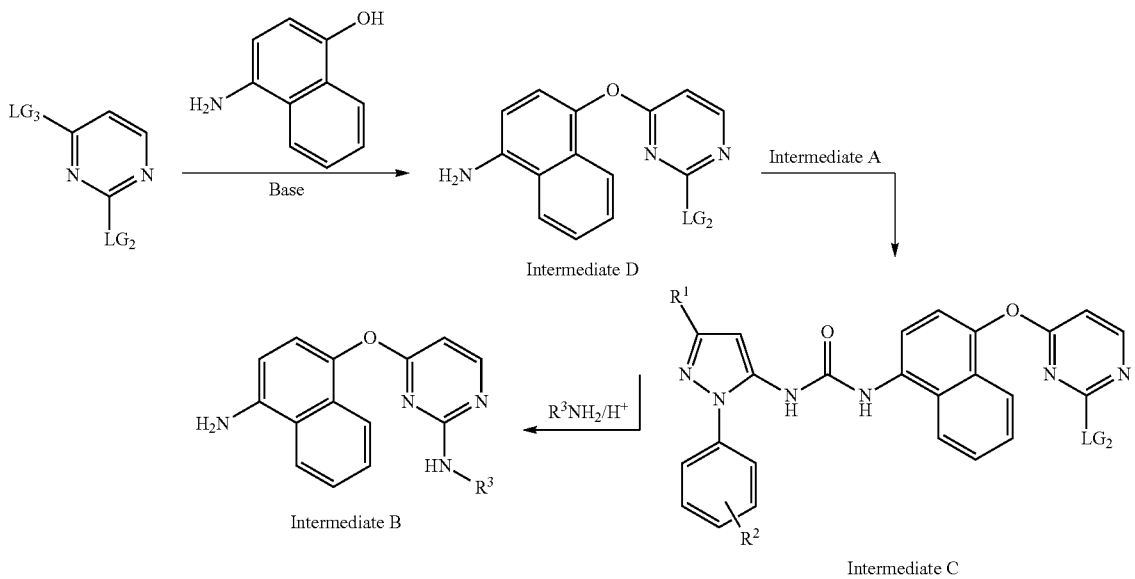

Scheme 2

The common precursors represented by Intermediate D are, in turn, readily prepared by a regioselective $S_NAr$ displacement reaction between a suitably functionalised pyrimidine and 4-aminonaphthalen-1-ol, in which $LG_3$ is leaving group, such as a halogen atom, for example chlorine. The reaction is conveniently carried out in the presence of a base such as triethylamine and in a non polar, aprotic solvent such as dicloromethane. The pyrimidine starting materials are either commercially available or are readily prepared by synthetic protocols that are well established in the art, Protective groups may be required to protect chemically sensitive groups during one or more of the reactions described above, to ensure that the process can be carried out and/or is efficient. Thus if desired or necessary, intermediate compounds may be protected by the use of conventional protective groups. Protective groups and the means for their removal are described in "Protective Groups in Organic Synthesis", by Theodora W. Greene and Peter G. M. Wuts, published by John Wiley & Sons Inc; 4th Rev Ed., 2006, ISBN-10: 0471697540.

Novel intermediates as described herein form an aspect of the invention.

The compounds of formula (I) are p38 MAP kinase inhibitors (especially of the alpha subtype) and in one aspect the compounds are useful in the treatment of inflammatory diseases, for example COPD and/or asthma.

In one embodiment the compounds of formula (I) do not strongly inhibit GSK 3α, for example they have an $IC_{50}$ against GSK 3α of 1500 nM or greater; such as 2,000, 3,000, 4,000, 5,000, 6,000, 7,000, 8,000, 9,000 or 10,000 nM or greater.

Persistence of action as used herein is related to the dissociation rate or dissociation constant of the compound from the target (such as a receptor). A low dissociation rate may lead to persistence.

A low dissociation rate in combination with a high association rate tends to provide potent therapeutic entities.

The compounds of formula (I) are expected to be potent in vivo.

Typically, the prior art compounds developed to date have been intended for oral administration. This strategy involves optimizing compounds which achieve their duration of action by an appropriate pharmacokinetic profile. This ensures that a sufficiently high drug concentration is established and maintained between doses to provide clinical benefit. The inevitable consequence of this approach is that all bodily tissues, and especially the liver and the gut, are likely to be exposed to supra-therapeutically active concentrations of the drug, whether or not they are adversely affected by the disease being treated.

An alternative strategy is to design treatment paradigms in which the drug is dosed directly to the inflamed organ (topical therapy). While this approach is not suitable for treating all chronic inflammatory diseases, it has been extensively exploited in lung diseases (asthma, COPD), skin diseases (atopic dermatitis and psoriasis), nasal diseases (allergic rhinitis) and gastrointestinal diseases (ulcerative colitis).

In topical therapy, efficacy can be achieved either by (i) ensuring that the drug has a sustained duration of action and is retained in the relevant organ to minimize the risks of systemic toxicity or (ii) producing a formulation which generates a "reservoir" of the active drug which is available to sustain the drug's desired effects. Approach (i) is exemplified by the anticholinergic drug tiotropium (Spiriva), which is administered topically to the lung as a treatment for COPD, and which has an exceptionally high affinity for its target receptor, resulting in a very slow off rate and a consequent sustained duration of action.

In one aspect of the disclosure the compound of formula (I) is particularly suitable for topical delivery, such as topical delivery to the lungs, in particular for the treatment of respiratory disease, for example chronic respiratory diseases such as COPD and/or asthma.

In one embodiment the compound of formula (I) is suitable for sensitizing patients to treatment with a corticosteroid who have become refractory to such treatment regimens.

The compound of formula (I) may also be useful for the treatment of rheumatoid arthritis.

The compound of formula (I) may have antiviral properties, for example the ability to prevent infection of cells (such as respiratory epithelial cells) with a picornavirus, in particular a rhinovirus, influenza or respiratory synctial virus.

Thus the compound is thought to be an antiviral agent, in particular suitable for the prevention, treatment or amelioration of picornavirus infections, such as rhinovirus infection, influenza or respiratory syncitial virus.

In one embodiment the compound of formula (I) is able to reduce inflammation induced by viral infection, such as rhinovirus infection and in particular viral infections that result in the release of cytokines such as IL-8, especially in vivo. This activity may, for example, be tested in vitro employing a rhinovirus induced IL-8 assay as described in the Examples herein.

In one embodiment the compound of formula (I) is able to reduce ICAM1 expression induced by rhinovirus, especially in vivo. ICAM1 is the receptor mechanism used by so-called major groove rhinovirus serotypes to infect cells. This activity may be measured, for example by a method described in the Examples herein.

It is expected that the above properties render the compound of formula (I) particularly suitable for use in the treatment and/or prophylaxis of exacerbations of inflammatory diseases, in particular viral exacerbations, in patients with one or more of the following chronic conditions such as congestive heart failure, COPD, asthma, diabetes, cancer and/or in immunosuppressed patients, for example post-organ transplant.

In particular, the compound of formula (I) may be useful in the treatment of one or more respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis, especially asthma, and COPD (including chronic bronchitis and emphysema).

The compound of formula (I) may also be useful in the treatment of one or more conditions which may be treated by topical or local therapy including allergic conjunctivitis, conjunctivitis, allergic dermatitis, contact dermatitis, psoriasis, ulcerative colitis, inflamed joints secondary to rheumatoid arthritis or to osteoarthritis.

It is also expected that the compound of formula (I) may be useful in the treatment of certain other conditions including rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

The compound of formula (I) may be useful in the treatment of eye diseases or disorders including allergic conjunctivitis, conjunctivitis, diabetic retinopathy, macular oedema (including wet macular oedema and dry macular oedema), post-operative cataract inflammation or, particularly, uveitis (including posterior, anterior and pan uveitis).

The compound of formula (I) may be useful in the treatment of gastrointestinal diseases or disorders including ulcerative colitis or Crohn's disease.

The compound of formula (I) may also re-sensitise the patient's condition to treatment with a corticosteroid, when the patient's condition has become refractory to the same.

Furthermore, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably a compound of formula (I) is administered topically to the lung. Hence we provide according to the invention a pharmaceutical composition comprising a compound of the disclosure optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoro methane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean aerodynamic diameter (MMAD) of 1-10 μm. The formulation will typically contain a topically acceptable diluent such as lactose, usually of large particle size e.g. an MMAD of 100 μm or more. Examples of dry powder delivery systems include SPINHALER, DISKHALER, TURBOHALER, DISKUS and CLICKHALER.

A compound of formula (I) has therapeutic activity. In a further aspect, the present invention provides a compound of the disclosure for use as a medicament. Thus, in a further aspect, the present invention provides a compound as described herein for use in the treatment of one or more of the above mentioned conditions.

In a further aspect, the present invention provides use of a compound as described herein for the manufacture of a medicament for the treatment of one or more of the above mentioned conditions.

In a further aspect, the present invention provides a method of treatment of one or more of the above mentioned conditions which comprises administering to a subject an effective amount of a compound of the disclosure or a pharmaceutical composition comprising the compound.

The word "treatment" is intended to embrace prophylaxis as well as therapeutic treatment.

A compound of the disclosure may also be administered in combination with one or more other active ingredients e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol) and/or xanthines (e.g. theophylline). Other suitable actives include anticholinergics, such as tiotropium and anti-viral agents such as, but not limited to, zanamivir or oseltamivir, for example as the phosphate. Other anti-viral agents include peramivir and laninamivir.

The data generated below in relation to the antiviral properties of the compounds of formula (I) leads the inventors to believe that other antiviral therapies would be useful in the treatment or prevention of exacerbations suffered by patients with respiratory disease such as COPD and/or asthma and/or one or more of the indications listed above. Thus in one aspect there is provided the use of an anti-viral therapy, such as, but not limited to, zanamavir or oseltamivir (for example oseltamivir phosphate), in the treatment or prevention of respiratory viral infections in patients with chronic conditions such as congestive heart failure, diabetes, cancer, or in immunosuppressed patients, for example post-organ transplant.

EXPERIMENTAL SECTION

Abbreviations used herein are defined below (Table 1). Any abbreviations not defined are intended to convey their generally accepted meaning.

TABLE 1

| Abbreviations | |
|---|---|
| AcOH | glacial acetic acid |
| aq | aqueous |
| ATP | adenosine-5'-triphosphate |
| BALF | bronchoalveolae lavage fluid |
| br | broad |
| BSA | bovine serum albumin |
| CatCart ® | catalytic cartridge |
| CDI | 1,1-carbonyl-diimidazole |
| COPD | chronic obstructive pulmonary disease |
| d | doublet |
| DCM | dichloromethane |
| DMSO | dimethyl sulfoxide |
| d-U937 cells | PMA differentiated U-937 cells |
| (ES$^+$) | electrospray ionization, positive mode |
| Et | ethyl |
| EtOAc | ethyl acetate |
| FCS | foetal calf serum |
| FRET | fluorescence resonance energy transfer |
| GSK3α | glycogen synthase kinase 3α |
| HBEC | primary human bronchial epithelial cells |
| hr | hour(s) |
| HRP | horseradish peroxidise |
| HRV | human rhinovirus |
| ICAM-1 | inter-cellular adhesion molecule 1 |
| JNK | c-Jun N-terminal kinase |
| LPS | lipopolysaccharide |
| $(M + H)^+$ | protonated molecular ion |
| MAPK | mitogen protein activated protein kinase |
| MAPKAP-K2 | mitogen-activated protein kinase-activated protein kinase-2 |
| Me | methyl |
| MeCN | acetonitrile |
| MeOH | methanol |
| MHz | megahertz |
| MMAD | mass median aerodynamic diameter |
| MOI | multiplicity of infection |
| min | minute(s) |
| MTT | 3-(4,5-dimethylthiazol-2-yl)-2,5-diphenyltetrazolium bromide |
| m/z: | mass-to-charge ratio |
| NMR | nuclear magnetic resonance (spectroscopy) |
| PBMC | peripheral blood mononuclear cell |
| PBS | phosphate buffered saline |
| Ph | phenyl |
| PHA | phytohaemagglutinin |
| PMA | phorbol myristate acetate |
| pTSA | 4-methylbenzenesulfonic acid |
| q | quartet |
| RT | room temperature |
| RP HPLC | reverse phase high performance liquid chromatography |
| RSV | respiratory syncytical virus |
| s | singlet |
| sat | saturated |
| SCX | solid supported cation exchange (resin) |
| SDS | sodium dodecyl sulphate |
| $S_NAr$ | nucleophilic aromatic substitution |
| t | triplet |
| TBDMS | tert-butyldimethylsilyl |
| TCID$_{50}$ | 50% tissue culture infectious dose |

TABLE 1-continued

| | Abbreviations |
|---|---|
| THF | tetrahydrofuran |
| TNFα | tumor necrosis factor alpha |

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 μm) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Preparative Reverse Phase High Performance Liquid Chromatography:

Agilent Scalar column C18, 5 μm (21.2×50 mm), flow rate 28 mL min$^{-1}$ eluting with a $H_2O$-MeCN gradient containing 0.1% v/v formic acid over 10 min using UV detection at 215 and 254 nm. Gradient information: 0.0-0.5 min; 95% $H_2O$-5% MeCN; 0.5-7.0 min; ramped from 95% $H_2O$-5% MeCN to 5% $H_2O$-95% MeCN; 7.0-7.9 min; held at 5% $H_2O$-95% MeCN; 7.9-8.0 min; returned to 95% $H_2O$-5% MeCN; 8.0-10.0 min; held at 95% $H_2O$-5% MeCN.

Analytical Methods

Reverse Phase High Performance Liquid Chromatography:

(Method 1): Agilent Scalar column C18, 5 μm (4.6×50 mm) or Waters XBridge C18, 5 μm (4.6×50 mm) flow rate 2.5 mL min$^{-1}$ eluting with a $H_2O$-MeCN gradient containing either 0.1% v/v formic acid (Method 1 acidic) or $NH_3$ (Method 1 basic) over 7 min employing UV detection at 215 and 254 nm. Gradient information: 0.0-0.1 min, 95% $H_2O$-5% MeCN; 0.1-5.0 min, ramped from 95% $H_2O$-5% MeCN to 5% $H_2O$-95% MeCN; 5.0-5.5 min, held at 5% $H_2O$-95% MeCN; 5.5-5.6 min, held at 5% $H_2O$-95% MeCN, flow rate increased to 3.5 mL min$^{-1}$; 5.6-6.6 min, held at 5% $H_2O$-95% MeCN, flow rate 3.5 mL min$^{-1}$; 6.6-6.75 min, returned to 95% $H_2O$-5% MeCN, flow rate 3.5 mL min$^{-1}$; 6.75-6.9 min, held at 95% $H_2O$-5% MeCN, flow rate 3.5 mL·min$^{-1}$; 6.9-7.0 min, held at 95% $H_2O$-5% MeCN, flow rate reduced to 2.5 mL Reverse Phase High Performance Liquid Chromatography:

Method 2: Agilent Extend C18 column, 1.8 μm (4.6×30 mm) at 40° C.; flow rate 2.5-4.5 mL min$^{-1}$ eluting with a $H_2O$-MeCN gradient containing 0.1% v/v formic acid over 4 min employing UV detection at 254 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL min$^{-1}$; 3.01 3.50 min, held at 5% $H_2O$-95% MeCN; 3.50-3.60 min, returned to 95% $H_2O$-5% MeCN, flow rate reduced to 3.50 mL min$^{-1}$; 3.60-3.90 min, held at 95% $H_2O$-5% MeCN; 3.90-4.00 min, held at 95% $H_2O$-5% MeCN, flow rate reduced to 2.5 mL min$^{-1}$.

$^1$H NMR Spectroscopy:

$^1$H NMR spectra were acquired on a Bruker Avance III spectrometer at 400 MHz using residual undeuterated solvent as reference and unless specified otherwise were run in DMSO-d$_6$.

The following intermediates used to prepare Compound (I) of the invention have been previously described and were prepared using the procedures contained in the references cited below (Table 2).

TABLE 2

Previously Described Intermediates.

| Intermediate | Structure | Name, LCMS Data and Reference |
|---|---|---|
| A1 | $^t$Bu-pyrazole with N-p-tolyl and 5-NH$_2$ | 3-tert-butyl-1-p-tolyl-1H-pyrazol-5-amine. R$^t$ 2.46 min (Method 1 basic); m/z 230 (M + H)$^+$, (ES$^+$). Cirillo, P. F. et al., WO 2000/43384, 27 Jul. 2000. |
| A2 | $^t$Bu-pyrazole with N-(4-methoxyphenyl) and 5-NH$_2$ | 3-tert-butyl-1-(4-methoxyphenyl)-1H-pyrazol-5-amine. R$^t$ 1.32 min (Method 2); m/z 246 (M + H)$^+$, (ES$^+$). Mathias, J. P. et al., US 2006/0035922, 10 Aug. 2005. |

TABLE 2-continued

Previously Described Intermediates.

| Intermediate | Structure | Name, LCMS Data and Reference |
| --- | --- | --- |
| A3 | 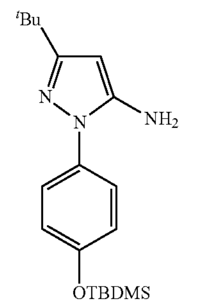 [SMILES: CC(C)(C)c1cc(N)n(-c2ccc(O[Si](C)(C)C(C)(C)C)cc2)n1] | 3-tert-butyl-1-(4-(tert-butyldimethylsilyloxy)phenyl)-1H-pyrazol-5-amine. $R^t$ 2.80 min (Method 2); m/z 346 (M + H)$^+$, (ES$^+$). Mathias, J. P. et al., US 2006/0035922, 10 Aug. 2005. |
| D1 | 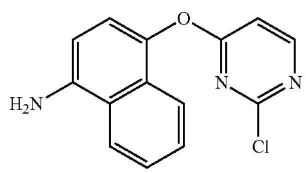 [SMILES: Nc1ccc(Oc2ccnc(Cl)n2)c2ccccc12] | 4-((2-chloropyrimidin-4-yl)oxy)naphthalen-1-amine. $R^t$ 1.80 min (Method 2); m/z 272/274 (M + H)$^+$, (ES$^+$). Cirillo, P. F. et al., WO 2002/92576, 21 Nov. 2000. |

Intermediate B1: 4-((4-Aminonaphthalen-1-yl)oxy)-N-phenylpyrimidin-2-amine

Intermediate C1: 1-(3-(tert-Butyl)-1-(p-tolyl)-1H-pyrazol-5-yl)-3-(4-((2-chloropyrimidin-4-yl)oxy)naphthalen-1-yl)urea

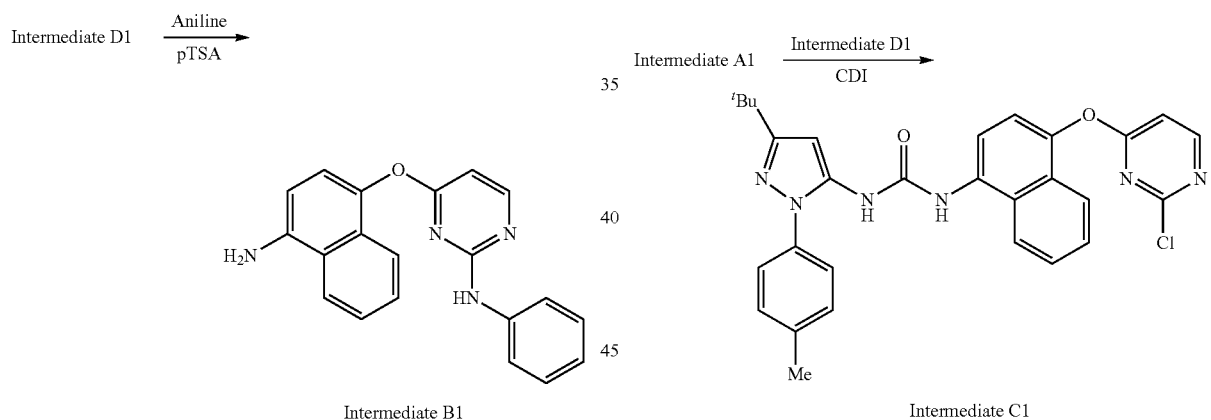

To a nitrogen purged solution of mixture of Intermediate D1 (50.0 g, 184 mmol) and aniline (42.0 mL, 460 mmol) in THF (200 mL) was added pTSA (17.5 g, 92.0 mmol) in a single portion. The reaction mixture was heated to 70° C. for 1.5 hr during which time which a precipitate formed. The mixture was cooled to RT and diluted with THF (200 mL). The precipitate was collected by filtration, washed with THF (2×100 mL) and then suspended in a heterogeneous mixture of DCM (600 mL) and aq. NaOH (2M, 200 mL) and stirred vigorously for 1 hr, during which time the suspended solids dissolved. The layers were separated and the aq layer was extracted with DCM (200 mL). The DCM extracts were combined, dried and evaporated in vacuo. The residue was triturated with ether (150 mL) and the resulting solid was washed with ether (2×50 mL) to afford Intermediate B1 as an off white solid (26 g, 43%); IV 1.95 min (Method 2); m/z 329 (WH)$^+$ (ES$^+$).

To a suspension of CDI (4.81 g, 29.7 mmol) in DCM (60 mL) was added Intermediate A1 (8.50 g, 29.7 mmol) portion-wise. After 3 hr an aliquot of this solution containing the activated CDI adduct, (30 mL, 15 mmol) was added to a solution of Intermediate D1 (3.01 g, 9.97 mmol) in DCM (60 mL) and the reaction mixture maintained at RT. After 2 hr a second aliquot of the CDI adduct solution (6.0 mL, 6.0 mmol) was added and the reaction mixture kept at RT for a further 16 hr. The resulting mixture was diluted with DCM (100 mL) and washed with saturated aq. NaHCO$_3$ (100 mL) and water (2×100 mLI) and then dried and evaporated in vacuo. The residue was purified by flash column chromatography (SiO$_2$, [10% MeOH in DCM] in DCM, 0-100%, gradient elution then SiO$_2$, EtOAc in isohexane, 0-100%, gradient elution) to afford the title compound, Intermediate C1 as a yellow solid (3.07 g, 55%); IR' 2.59 min (Method 2); m/z 527/529 (M+H)$^+$ (ES$^+$).

Example 1

1-(3-(tert-Butyl)-1-(p-tolyl)-1H-pyrazol-5-yl)-3-(4-(2-(phenylamino)pyrimidin-4-yloxy)naphthalen-1-yl)urea Intermediate A1 →(1. PhOC(O)Cl, 2. Intermediate B1)

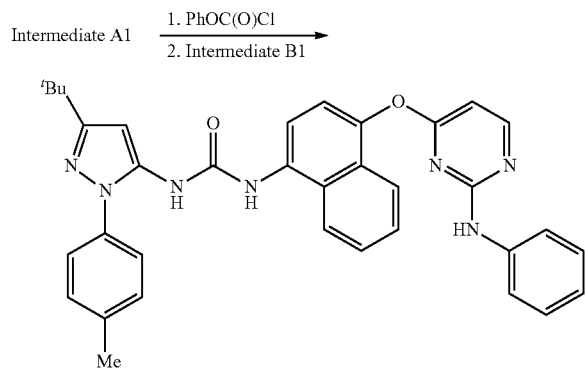

Example 1

A heterogeneous mixture of a solution of Na₂CO₃ (3.84 g, 36 mmol) in water (42 mL) and Intermediate A1 (10.5 g, 45.7 mmol) in isopropyl acetate (130 mL, 1.082 mol) was stirred vigorously at RT for 5 min and was then treated with phenyl carbonochloridate (5.77 ml, 45.7 mmol). Stirring of the mixture was continued for a further 4 hr after which the layers were separated. The organic phase was added to a solution of Intermediate B1 (10.0 g, 30.5 mmol) and triethylamine (423 µL, 3.05 mmol) in ispropyl acetate (60 mL, 511 mmol). The reaction mixture was warmed to 48° C. for 1 hr, then diluted with isopropyl acetate (190 mL) and cooled to RT for a further 18 hr, during which time a precipitate formed. The precipitate was isolated by filtration, washed with isopropyl acetate and then dried in vacuo at 40° C. to afford the title compound, Example 1 as a white solid (16.5 g, 92%); R' 2.74 min (Method 2); m/z 584 (M+1-1)⁺ (ES⁺); ¹H NMR (400 MHz, DMSO-d₆) δ: 1.30 (9H, s), 2.41 (3H, s), 6.43 (1H, s), 6.58 (1H, d), 6.78 (1H, t), 6.97 (2H, t), 7.28 (2H, br m), 7.39 (2H, d), 7.40 (1H, d), 7.49 (2H, d), 7.56 (1H, m), 7.63 (1H, m), 7.82 (1H, dd), 7.95 (1H, d), 8.10 (1H, d), 8.40 (1H, d), 8.77 (1H, s), 9.16 (1H, br s), 9.50 (1H, br s).

Example 2

1-(3-(tert-Butyl)-1-(p-tolyl)-1H-pyrazol-5-yl)-3-(4-((2-((3-hydroxyphenyl)amino)pyrimidin-4-yl)oxy)naphthalen-1-yl)urea Intermediate C1 →(pTSA) 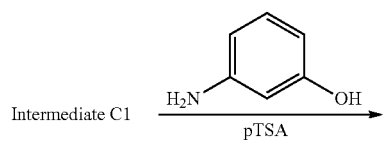

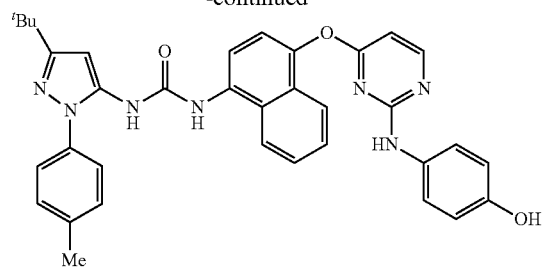

Example 2

To a solution of Intermediate C1 (150 mg, 0.285 mmol) in DMF (2.0 mL) were added 3-aminophenol (52 mg, 0.477 mmol) and pTSA (96 mg, 0.51 mmol) and the resulting dark solution was heated to 60° C. for 16 hr. The reaction mixture was cooled to RT and was then partitioned between EtOAc (20 mL) and saturated aq. NaHCO₃ (20 mL). The organic phase was separated and washed sequentially with saturated aq. NaHCO₃ (20 mL), water (20×20 mL) and brine (2×20 mL) and was then dried and evaporated in vacuo. The residue was purified by flash column chromatography (SiO₂, 40 g, EtOAc in isohexane, 0-100%, gradient elution) and the partially purified product so obtained was triturated with IPA to afford the title compound, Example 2, as an off white solid (56 mg, 32%); IR' 2.52 min (Method 2); m/z 600 (M+1-1)⁺ (ES⁺); ¹H NMR (400 MHz, DMSO-d₆) ä: 1.29 (9H, s), 2.40 (3H, s), 6.24 (1H, dd), 6.41 (1H, s), 6.47 (1H, d), 6.74 (1H, br t), 6.82 (1H, br d), 6.99 (1H, br s), 7.38-7.39 (3H, overlapping m), 7.46 (2H, d), 7.56 (1H, dt), 7.62 (1H, dt), 7.81 (1H, dd), 7.92 (1H, d), 8.07 (1H, d), 8.35 (1H, d), 8.74 (1H, s), 9.12 (2H, s), 9.36 (1H, s).

Example 3

1-(3-(tert-butyl)-1-(4-hydroxyphenyl)-1H-pyrazol-5-yl)-3-(4-((2-(phenylamino) pyrimidin-4-yl)oxy)naphthalen-1-yl)urea Intermediate A3 →(1. CDI, 2. Intermediate B1)

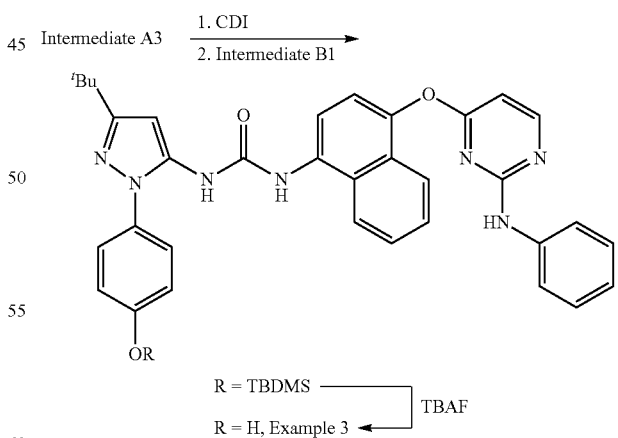

R = TBDMS ⎤
            ⎬ TBAF
R = H, Example 3 ⎦

To a solution of CDI (148 mg, 0.914 mmol) in DCM (2.0 mL) at RT was added Intermediate A3 (316 mg, 0.914 mmol). After 2 hr an aliquot of the resulting solution (1.0 mL, 0.50 mmol), was added to a solution of Intermediate B1 (100 mg, 0.305 mmol) in THF (3.0 mL) and the reaction mixture maintained at RT for 18 hr and then partitioned between DCM (25 mL) and saturated aq. NaHCO$_3$ (25 mL). The aq. layer was separated and was extracted with DCM (25 mL) and the combined organic extracts were dried and evaporated in vacuo. The residue was purified by flash column chromatography (SiO$_2$, 12 g, EtOAc in isohexane, 20%-100%, gradient elution) and the impure product so obtained was triturated with MeOH to afford 1-(3-(tert-butyl)-1-(4-((tert-butyldimethylsilyl)oxy)phenyl)-1H-pyrazol-5-yl)-3-(4-((2-(phenylamino) pyrimidin-4-yl)oxy)naphthalen-1-yl)urea as an off white solid (70 mg, 33%); IV 3.74 min (Method 2); m/z 700 (M-FH)$^+$ (ES$^+$).

To a solution of the TBDMS protected intermediate obtained above (70 mg, 0.100 mmol) in THF (1.0 mL) was added TBAF (1 M solution in THF, 120 μL, 0.12 mmol) and the reaction mixture kept at RT for 1 hr and then partitioned between DCM (50 mL) and saturated aq. NaHCO$_3$ (50 mL). The aq. layer was separated and was extracted with DCM (50 mL) and the combined organic extracts were dried and evaporated in vacuo. The residue was purified by SCX capture and release to afford the title compound, Example 3, as an off white solid (25 mg, 41%); R$^r$ 2.38 min (Method 2); m/z 586 (M+H)$^+$ (ES$^+$); $^1$H NMR (400 MHz, DMSO-d$_6$) ä: 1.28 (9H, s), 6.38 (1H, s), 6.57 (1H, d), 6.77 (1H, t), 6.94-6.96 (4H, overlapping m), 7.26-7.28 (2H, overlapping m), 7.35 (2H, d), 7.39 (1H, d), 7.55 (1H, dt), 7.62 (1H, dt), 7.80 (1H, d), 7.94 (1H, d), 8.08 (1H, d), 8.38 (1H, d), 8.67 (1H, s), 9.16 (1H, s), 9.51 (1H, s), 9.81 (1H, s).

Additional Compound Examples of the Invention

| Ex. No. | Structure | Name and Analytical Data [Route] |
|---|---|---|
| 4 | 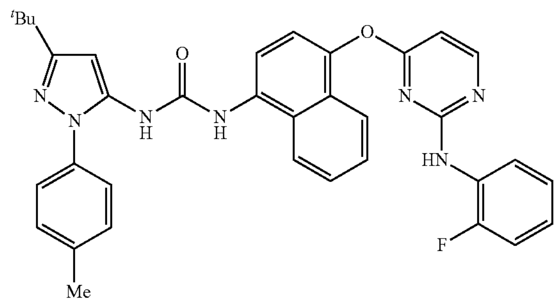 | 1-(3-(tert-butyl)-1-(p-tolyl)-1H-pyrazol-5-yl)-3-(4-((2-((2-fluorophenyl)amino)pyrimidin-4-yl)oxy)naphthalen-1-yl)urea. R$^r$ 2.85 min (Method 2); m/z 602 (M + H)$^+$ (ES$^+$); $^1$H NMR ä: 1.28 (9H, s), 2.40 (3H, s), 6.42 (1H, s), 6.51 (1H, d), 6.83 (1H, t), 6.99 (1H, m), 7.09 (1H, m), 7.29 (1H, dt), 7.37-7.39 (3H, overlapping m), 7.47 (2H, d), 7.57 (1H, dt), 7.63 (1H, dt), 7.81 (1H, dd), 7.90 (1H, d), 8.06 (1H, d), 8.31 (1H, d), 8.76 (1H, s), 9.01 (1H, s), 9.13 (1H, s). [B] |
| 5 | 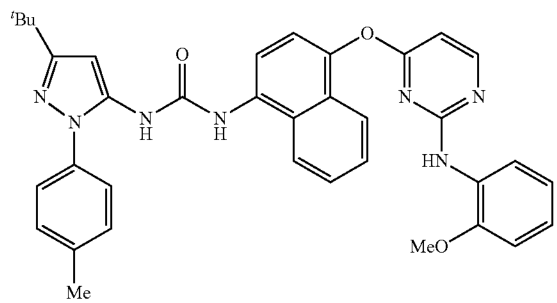 [SMILES: COc1ccccc1Nc1nccc(Oc2ccc(NC(=O)Nc3cc(C(C)(C)C)nn3-c3ccc(C)cc3)c3ccccc23)n1] | 1-(3-(tert-butyl)-1-(p-tolyl)-1H-pyrazol-5-yl)-3-(4-((2-((2-methoxyphenyl)amino)pyrimidin-4-yl)oxy)naphthalen-1-yl)urea. R$^r$ 2.84 min (Method 2); m/z 614 (M + H)$^+$ (ES$^+$); $^1$H NMR ä: 1.29 (9H, s), 2.40 (3H, s), 3.76 (3H, s) 6.42 (1H, s), 6.51 (1H, t), 6.56 (1H, d), 6.85 (1H, t), 6.91 (1H, dd), 7.38-7.43 (4H, overlapping m), 7.47 (2H, d), 7.56 (1H, dt), 7.62 (1H, dt), 7.81 (1H, dd), 7.86 (1H, s), 7.95 (1H, d), 8.09 (1H, d), 8.36 (1H, d), 8.76 (1H, s), 9.14 (1H, s). [B] |
| 6 | 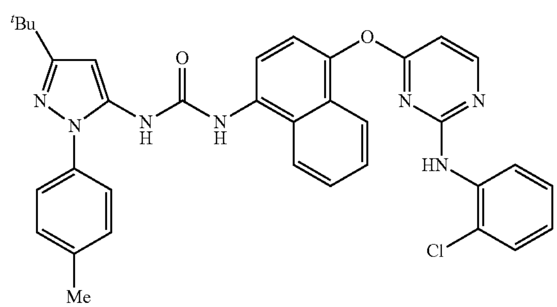 [SMILES: Cc1ccc(-n2nc(C(C)(C)C)cc2NC(=O)Nc2ccc(Oc3ccnc(Nc4ccccc4Cl)n3)c3ccccc23)cc1] | 1-(3-(tert-butyl)-1-(p-tolyl)-1H-pyrazol-5-yl)-3-(4-((2-((2-chlorophenyl)amino)pyrimidin-4-yl)oxy)naphthalen-1-yl)urea. R$^r$ 3.05 min (Method 2); m/z 618 (M + H)$^+$ (ES$^+$); $^1$H NMR ä: 1.29 (9H, s), 2.40 (3H, s), 6.42 (1H, s), 6.51 (1H, d), 6.99-7.01 (2H, overlapping m), 7.36-7.38 (5H, overlapping m), 7.46 (2H, d), 7.57 (1H, dt), 7.63 (1H, dt), 7.81 (1H,dd), 7.91 (1H,d), 8.07 (1H, d), 8.31 (1H, d), 8.65 (1H, s), 8.76 (1H, s), 9.12 (1H, s). [B] |
| 7 | 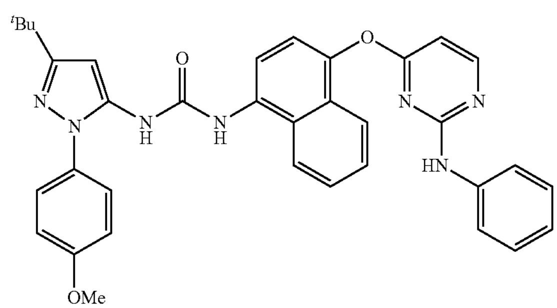 [SMILES: COc1ccc(-n2nc(C(C)(C)C)cc2NC(=O)Nc2ccc(Oc3ccnc(Nc4ccccc4)n3)c3ccccc23)cc1] | 1-(3-(tert-butyl)-1-(4-methoxyphenyl)-1H-pyrazol-5-yl)-3-(4-((2-(phenylamino)pyrimidin-4-yl)oxy)naphthalen-1-yl)urea. R$^r$ 2.69 min (Method 2); m/z 600 (M + H)$^+$ (ES$^+$): $^1$H NMR ä: 1.29 (9H, s), 3.84 (3H, s), 6.40 (1H, s), 6.57 (1H, d), 6.77 (1H, t), 6.96 (1H, t), 7.13 (2H, d), 7.27 (2H, d), 7.39 (1H, d), 7.49 (2H, d), 7.55 (1H, dt), 7.61 (1H, dt), 7.81 (1H, d), 7.94 (1H, d), 8.08 (1H, d), 8.38 (1H, d), 8.70 (1H, s), 9.13 (1H, s), 9.50 (1H, s). [B] |

| Ex. No. | Structure | Name and Analytical Data [Route] |
|---|---|---|
| 8 | 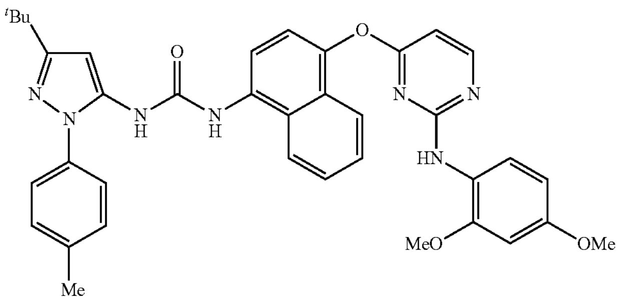 [SMILES: COc1ccc(Nc2nccc(Oc3ccc(NC(=O)Nc4cc(C(C)(C)C)nn4-c4ccc(C)cc4)c4ccccc34)n2)c(OC)c1] | 1-(3-(tert-butyl)-1-(p-tolyl)-1H-pyrazol-5-yl)-3-(4-((2-((2,4-dimethoxyphenyl)amino)pyrimidin-4-yl)oxy)naphthalen-1-yl)urea. R$^t$ 2.78 min (Method 2); m/z 644 (M + H)$^+$ (ES$^+$); 1H NMR ä: 1.29 (9H, s), 2.99 (3H, s), 3.67 (3H, s), 3.71 (3H, s), 6.19 (1H, d), 6.41 (1H, s), 6.46 (1H, d), 6.49 (1H, d), 7.18 (1H, d), 7.36 (1H, d), 7.39 (2H, d), 7.47 (2H, d), 7.55 (1H, dt), 7.61 (1H, dt), 7.80 (1H, d), 7.85 (1H, s), 7.92 (1H, d), 8.07 (1H, d), 8.28 (1H, d), 8.78 (1H, s), 9.14 (1H, s). [B] |
| 9 | 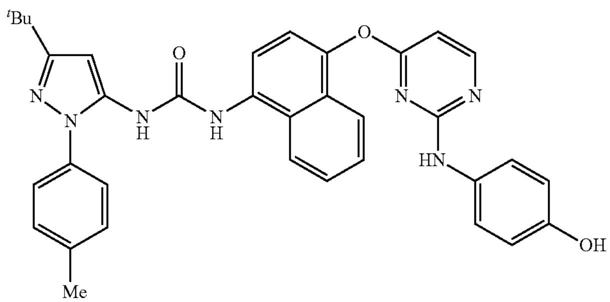 [SMILES: Cc1ccc(-n2nc(C(C)(C)C)cc2NC(=O)Nc2ccc(Oc3ccnc(Nc4ccc(O)cc4)n3)c3ccccc23)cc1] | 1-(3-(tert-butyl)-1-(p-tolyl)-1H-pyrazol-5-yl)-3-(4-((2-((4-hydroxyphenyl)amino)pyrimidin-4-yl)oxy)naphthalen-1-yl)urea. R$^t$ 2.42 min (Method 2); m/z 600 (M + H)$^+$ (ES$^+$); $^1$H NMR ä: 1.29 (9H, s), 2.40 (3H, s), 6.40-6.45 (4H, overlapping m), 7.08 (2H, br s), 7.36-7.39 (3H, overlapping m), 7.47 (2H, d), 7.55 (1H, dt), 7.62 (1H, dt), 7.80 (1H, d), 7.94 (1H, d), 8.08 (1H, d), 8.30 (1H, d), 8.82 (1H, s), 8.93 (1H, s), 9.17 (1H, s), 9.20 (1H, brs). [B] |
| 10 | 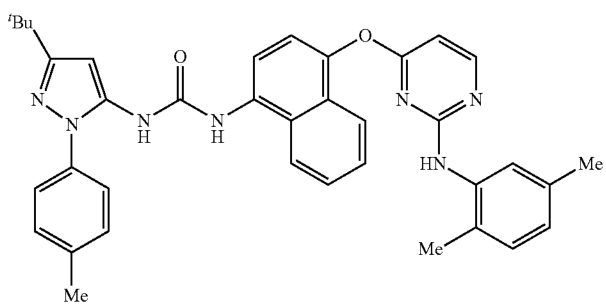 [SMILES: Cc1ccc(-n2nc(C(C)(C)C)cc2NC(=O)Nc2ccc(Oc3ccnc(Nc4cc(C)ccc4C)n3)c3ccccc23)cc1] | 1-(3-(tert-butyl)-1-(p-tolyl)-1H-pyrazol-5-yl)-3-(4-((2-((2,5-dimethylphenyl)amino)pyrimidin-4-yl)oxy)naphthalen-1-yl)urea. R$^t$ 2.91 min (Method 2); m/z 612 (M + H)$^+$ (ES$^+$); $^1$H NMR ä: 1.28 (9H, s), 2.00 (3H, s), 2.06 (3H, s), 2.39 (3H, s), 6.39-6.40 (2H, overlapping m), 6.72 (1H, d), 6.95-6.98 (2H, overlapping m), 7.35-7.38 (3H; overlapping m), 7.46 (2H, d) 7.57 (1H, dt), 7.62 (1H, dt), 7.81 (1H, d), 7.90 (1H, d), 8.06 (1H, d), 8.25 (1H, d), 8.58 (1H, s), 8.87 (1H, s), 9.18 (1H, s). [B] |
| 11 | 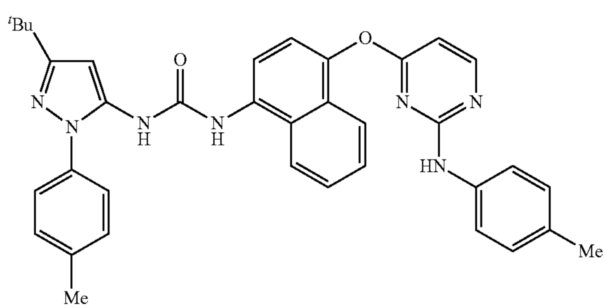 [SMILES: Cc1ccc(Nc2nccc(Oc3ccc(NC(=O)Nc4cc(C(C)(C)C)nn4-c4ccc(C)cc4)c4ccccc34)n2)cc1] | 1-(3-(tert-butyl)-1-(p-tolyl)-1H-pyrazol-5-yl)-3-(4-((2-(p-tolylamino)pyrimidin-4-yl)oxy)naphthalen-1-yl)urea. R$^t$ 2.81 min (Method 2); m/z 598 (M + H)$^+$ (ES$^+$); 1H NMR ä: 1.29 (9H, s), 2.13 (3H, s), 2.40 (3H, s), 6.43 (1H, s), 6.54 (1H, d), 6.80 (2H, d), 7.16 (2H, br s), 7.37-7.39 (3H, overlapping m) 7.47 (2H, d), 7.55 (1H, dt), 7.62 (1H, dt), 7.80 (1H, d), 7.92 (1H, d), 8.09 (1H, d), 8.37 (1H, d), 8.79 (1H, s), 9.16 (1H, s), 9.40 (1H, s). [B] |
| 12 | 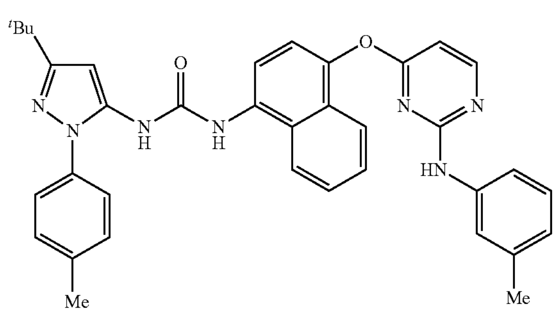 | 1-(3-(tert-butyl)-1-(p-tolyl)-1H-pyrazol-5-yl)-3-(4-((2-(m-tolylamino)pyrimidin-4-yl)oxy)naphthalen-1-yl)urea. R$^t$ 2.88 min (Method 2); m/z 598 (M + H)$^+$ (ES$^+$): $^1$H NMR ä: 1.29 (9H, s), 1.95 (3H, s), 2.40 (3H, s), 6.41 (1H, s), 6.57-6.60 (2H, overlapping m), 6.85 (1H, t), 7.04 (1H, br d), 7.11 (1H, br s) 7.37-7.40 (3H, overlapping m), 7.47 (2H, d), 7.55 (1H, dt), 7.62 (1H, dt), 7.80 (1H, d), 7.97 (1H, d), 8.09 (1H, d), 8.39 (1H, d), 8.82 (1H, s), 9.18 (1H, s), 9.46 (1H, s). [B] |

| Ex. No. | Structure | Name and Analytical Data [Route] |
|---|---|---|
| 13 | 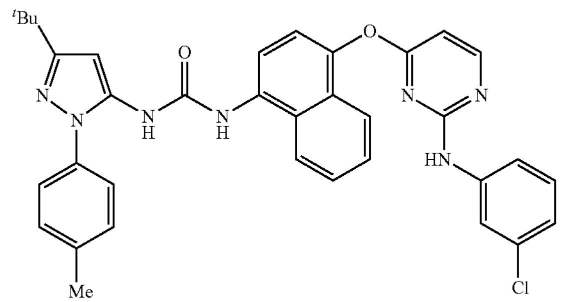 | 1-(3-(tert-butyl)-1-(p-tolyl)-1H-pyrazol-5-yl)-3-(4-((2-((3-chlorophenyl)amino)pyrimidin-4-yl)oxy)naphthalen-1-yl)urea. R$^t$ 2.95 min (Method 2); m/z 618 (M + H)$^+$ (ES$^+$); $^1$H NMR ä: 1.29 (9H, s), 2.40 (3H, s), 6.41 (1H, s), 6.65 (1H, d), 6.81 (1H, d), 7.00 (1H, t), 7.23 (1H, br d) 7.36-7.41 (3H, overlapping m), 7.46-7.49 (3H, overlapping m), 7.55 (1H, dt), 7.62 (1H, dt), 7.80 (1H, d), 7.96 (1H, d), 8.08 (1H, d), 8.46 (1H, d), 8.80 (1H, s), 9.14 (1H, s), 9.71 (1H, s). [B] |
| 14 | 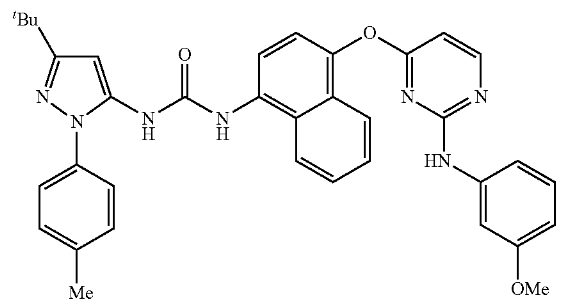 [SMILES: COc1cccc(Nc2nccc(Oc3ccc(NC(=O)Nc4cc(C(C)(C)C)nn4-c4ccc(C)cc4)c4ccccc34)n2)c1] | 1-(3-(tert-butyl)-1-(p-tolyl)-1H-pyrazol-5-yl)-3-(4-((2-((3-methoxyphenyl)amino)pyrimidin-4-yl)oxy)naphthalen-1-yl)urea. R$^t$ 2.74 min (Method 2); m/z 614 (M + H)$^+$ (ES$^+$); $^1$H NMR ä: 1.29 (9H, s), 2.40 (3H, s), 3.52 (3H, s), 6.38 (1H, dd), 6.42 (1H, s), 6.56 (1H, d), 6.88-6.95 (2H, overlapping m), 7.08 (1H, br s) 7.37-7.40 (3H, overlapping m), 7.47 (2H, d), 7.55 (1H, dt), 7.62 (1H, dt), 7.81 (1H, d), 7.95 (1H, d), 8.08 (1H, d), 8.39 (1H, d), 8.78 (1H, s), 9.14 (1H, s), 9.48 (1H, s). [B] |
| 15 | 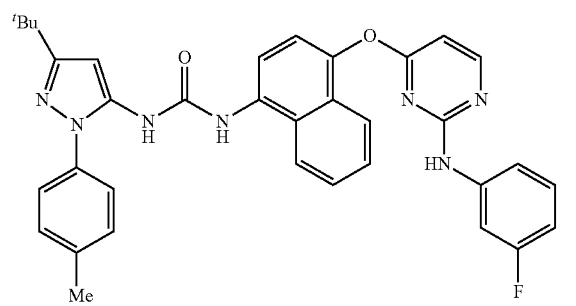 [SMILES: Cc1ccc(-n2nc(C(C)(C)C)cc2NC(=O)Nc2ccc(Oc3ccnc(Nc4cccc(F)c4)n3)c3ccccc23)cc1] | 1-(3-(tert-butyl)-1-(p-tolyl)-1H-pyrazol-5-yl)-3-(4-((2-((3-fluorophenyl)amino)pyrimidin-4-yl)oxy)naphthalen-1-yl)urea. R$^t$ 2.80 min (Method 2); m/z 602 (M + H)$^+$ (ES$^+$); $^1$H NMR ä: 1.29 (9H, s), 2.40 (3H, s), 6.42 (1H, s), 6.57 (1H, dt), 6.65 (1H, d), 7.02 (1H, q), 7.24 (1H, br d) 7.37-7.41 (3H, overlapping m), 7.48 (2H, d), 7.55 (1H, dt), 7.62 (1H, dt), 7.80 (1H, dd), 7.96 (1H, d), 8.10 (1H, d), 8.45 (1H, d), 8.84 (1H, s), 9.19 (1H, s), 9.74 (1H, s). [B] |
| 16 | 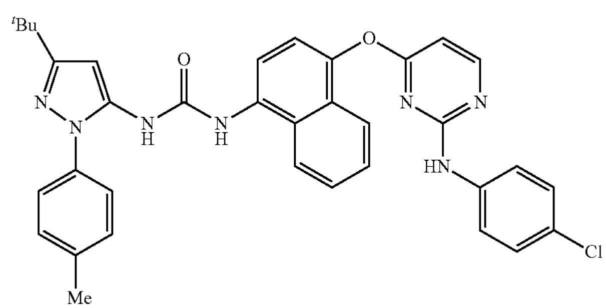 [SMILES: Cc1ccc(-n2nc(C(C)(C)C)cc2NC(=O)Nc2ccc(Oc3ccnc(Nc4ccc(Cl)cc4)n3)c3ccccc23)cc1] | 1-(3-(tert-butyl)-1-(p-tolyl)-1H-pyrazol-5-yl)-3- (4-((2-((4-chlorophenyl)amino)pyrimidin-4-yl)oxy)naphthalen-1-yl)urea. R$^t$ 2.90 min (Method 2); m/z 618 (M + H)$^+$ (ES$^+$); $^1$H NMR ä: 1.28 (9H, s), 2.40 (3H, s), 6.46 (1H, s), 6.65 (1H, d), 6.65 (1H, d), 7.04 (2H, d), 7.27 (1H, br d) 7.37-7.42 (3H, overlapping m), 7.48 (2H, d), 7.55 (1H, dt), 7.62 (1H, dt), 7.80 (1H, dd), 7.90 (1H, d), 8.08 (1H, d), 8.41 (1H, d), 8.79 (1H, s), 9.17 (1H, s), 9.70 (1H, s). [B] |
| 17 | 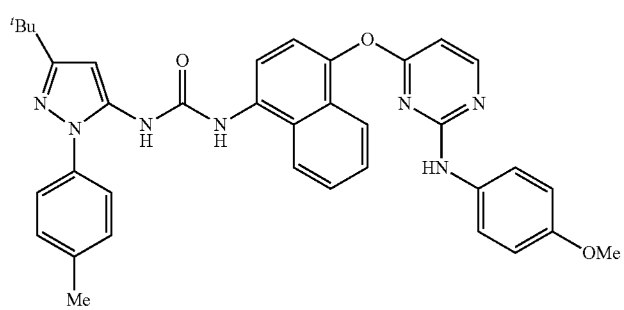 [SMILES: COc1ccc(Nc2nccc(Oc3ccc(NC(=O)Nc4cc(C(C)(C)C)nn4-c4ccc(C)cc4)c4ccccc34)n2)cc1] | 1-(3-(tert-butyl)-1-(p-tolyl)-1H-pyrazol-5-yl)-3-(4-((2-((4-methoxyphenyl)amino)pyrimidin-4-yl)oxy)naphthalen-1-yl)urea. R$^t$ 2.66 min (Method 2); m/z 614 (M + H)$^+$ (ES$^+$); 1H NMR ä: 1.29 (9H, s), 2.40 (3H, s), 3.62 (3H, s), 6.40 (1H, s), 6.52 (1H, d), 6.58 (2H, d), 7.15 (2H, br s), 7.37-7.39 (3H, overlapping m), 7.47 (2H, d), 7.54 (1H, dt), 7.61 (1H, dt), 7.80 (1H, dd), 7.91 (1H, d), 8.08 (1H, d), 8.34 (1H, d), 8.83 (1H, s), 9.20 (1H, s), 9.32 (1H, s). [B] |

| Ex. No. | Structure | Name and Analytical Data [Route] |
|---|---|---|
| 18 | 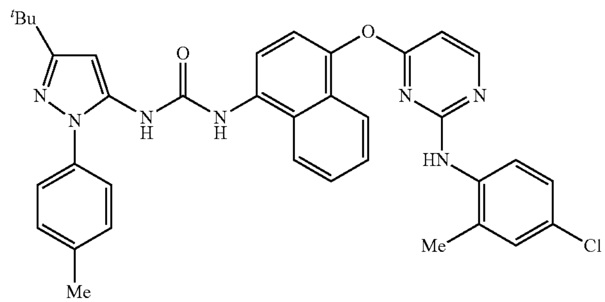 [SMILES: Cc1ccc(-n2nc(C(C)(C)C)cc2NC(=O)Nc2ccc(Oc3ccnc(Nc4ccc(Cl)cc4C)n3)c3ccccc23)cc1] | 1-(3-(tert-butyl)-1-(p-tolyl)-1H-pyrazol-5-yl)-3-(4-((2-((4-chloro-2-methylphenyl)amino)pyrimidin-4-yl)oxy)naphthalen-1-yl)urea. R$^t$ 2.95 min (Method 2); m/z 632 (M + H)$^+$ (ES$^+$): $^1$H NMR ä: 1.28 (9H, s), 2.11 (3H, s), 2.40 (3H, s), 6.42 (1H, s), 6.44 (1H, d), 6.91 (1H, dd), 7.15-7.17 (2H, overlapping m), 7.35-7.38 (3H, overlapping m), 7.47 (2H, d), 7.57 (1H, dt), 7.63 (1H, dt), 7.80 (1H, dd), 7.88 (1H, d), 8.06 (1H, d), 8.27 (1H, d), 8.73 (2H, d), 9.09 (1H, s). [B] |
| 19 | 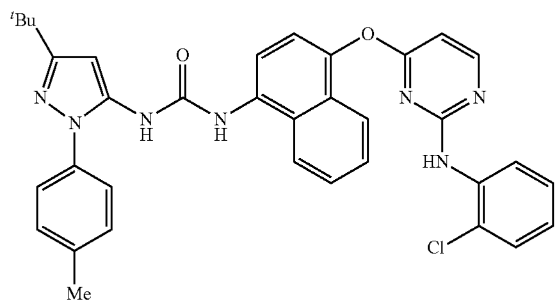 [SMILES: Cc1ccc(-n2nc(C(C)(C)C)cc2NC(=O)Nc2ccc(Oc3ccnc(Nc4ccccc4Cl)n3)c3ccccc23)cc1] | 1-(3-(tert-butyl)-1-(p-tolyl)-1H-pyrazol-5-yl)-3- (4-((2-((2-chlorophenyl)amino)pyrimidin-4-yl)oxy)naphthalen-1-yl)urea. R$^t$ 3.04 min (Method 2); m/z 662, 664 (M + H)$^+$ (ES$^+$); 1H NMR ä: 1.29 (9H, s), 2.39 (3H, s), 6.41 (1H, s), 6.49 (1H, d), 6.95 (1H, dt), 7.05 (1H, dt), 7.35-7.39 (4H, overlapping m), 7.46 (2H, d), 7.54-7.59 (2H, overlapping m), 7.63 (1H, dt), 7.81 (1H, dd), 7.90 (1H, d), 8.07 (1H, d), 8.31 (1H, d), 8.54 (1H, s), 8.79 (1H, s), 9.15 (1H, s). [B] |
| 20 | 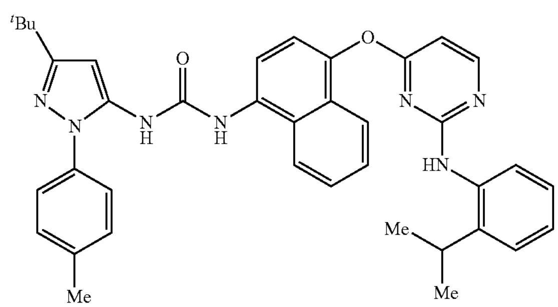 [SMILES: Cc1ccc(-n2nc(C(C)(C)C)cc2NC(=O)Nc2ccc(Oc3ccnc(Nc4ccccc4C(C)C)n3)c3ccccc23)cc1] | 1-(3-(tert-butyl)-1-(p-tolyl)-1H-pyrazol-5-yl)-3-(4-((2-((2-isopropylphenyl)amino)pyrimidin-4-yl)oxy)naphthalen-1-yl)urea. R$^t$ 2.92 min (Method 2); m/z 626 (M + H)$^+$ (ES$^+$); 1H NMR ä: 1.07 (6H, d), 1.29 (9H, s), 2.39 (3H, s), 3.09 (1H, m) 6.26 (1H, d), 6.38 (1H, s), 7.00 (1H, dt), 7.09-7.12 (2H, overlapping m), 7.24 (1H, dd), 7.34-7.36 (3H, overlapping m), 7.47 (2H, d), 7.57-7.64 (2H, overlapping m), 7.81 (1H, d), 7.85 (1H, d), 8.08 (1H, d), 8.16 (1H, d), 8.72 (1H, s), 9.03 (1H, s), 9.33 (1H, s). [B] |
| 21 | 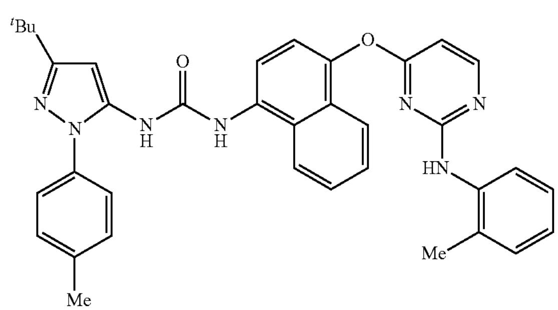 | 1-(3-(tert-butyl)-1-(p-tolyl)-1H-pyrazol-5-yl)-3-(4-((2-(o-tolylamino)pyrimidin-4-yl)oxy)naphthalen-1-yl)urea. R$^t$ 2.78 min (Method 2); m/z 598 (M + H)$^+$ (ES$^+$): $^1$H NMR ä: 1.29 (9H, s), 2.12 (3H, s), 2.39 (3H, s) 6.36 (1H, d), 6.40 (1H, s), 6.89-6.94 (2H, overlapping m), 7.09 (1H, d), 7.15 (1H, d), 7.35-7.37 (3H, overlapping m), 7.47 (2H, d), 7.57-7.64 (2H, overlapping m), 7.82 (1H, d), 7.87 (1H, d), 8.07 (1H, d), 8.24 (1H, d), 8.66 (1H, s), 8.88 (1H, s), 9.21 (1H, s). [B] |
| 22 | 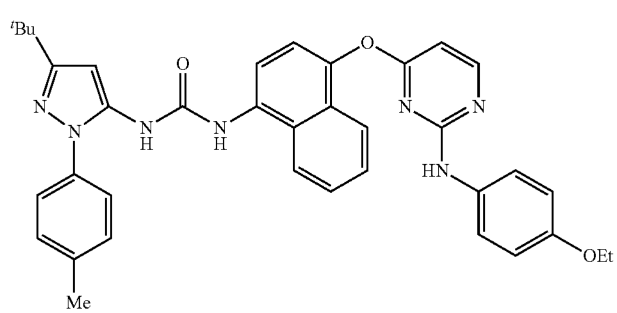 [SMILES: CCOc1ccc(Nc2nccc(Oc3ccc(NC(=O)Nc4cc(C(C)(C)C)nn4-c4ccc(C)cc4)c4ccccc34)n2)cc1] | 1-(3-(tert-butyl)-1-(p-tolyl)-1H-pyrazol-5-yl)-3- (4-((2-((4-ethoxyphenyl)amino)pyrimidin-4-yl)oxy)naphthalen-1-yl)urea. R$^t$ 2.80 min (Method 2); m/z 628 (M + H)$^+$ (ES$^+$) $^1$H NMR ä: 1.20 (3H, t), 1.29 (9H, s), 2.40 (3H, s), 3.85 (2H, q), 6.42 (1H, s), 6.52-6.56 (3H, overlapping m), 7.12 (2H, br s), 7.37-7.39 (3H, overlapping m), 7.47 (2H, d), 7.55 (1H, t), 7.61 (1H, t), 7.80 (1H, d), 7.93 (1H, d), 8.08 (1H, d), 8.33 (1H, d), 8.78 (1H, s), 9.16 (1H, s), 9.32 (1H, s). [B] |

-continued

| Ex. No. | Structure | Name and Analytical Data [Route] |
|---|---|---|
| 23 | 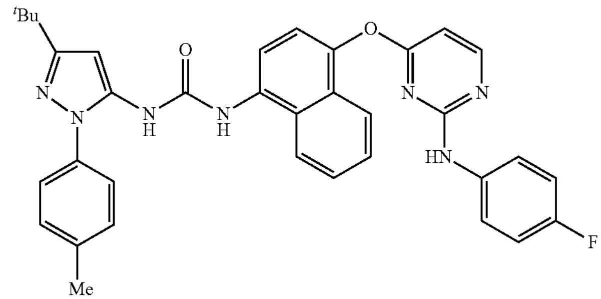 [SMILES: Cc1ccc(-n2nc(C(C)(C)C)cc2NC(=O)Nc2ccc(Oc3ccnc(Nc4ccc(F)cc4)n3)c3ccccc23)cc1] | 1-(3-(tert-butyl)-1-(p-tolyl)-1H-pyrazol-5-yl)-3-(4-((2-((4-fluorophenyl)amino)pyrimidin-4-yl)oxy)naphthalen-1-yl)urea. R$^t$ 2.83 min (Method 2); m/z 602 (M + H)$^+$ (ES$^+$); $^1$H NMR ä: 1.29 (9H, s), 2.39 (3H, s), 6.42 (1H, s), 6.59 (1H, d), 6.82 (2H, br t), 7.26 (2H, br s), 7.37-7.39 (3H, overlapping m), 7.47 (2H, d), 7.55 (1H, dt), 7.60 (1H, dt), 7.79 (1H, dd), 7.89 (1H, d), 8.08 (1H, d), 8.38 (1H, d), 8.84 (1H, s), 9.22 (1H, s), 9.56 (1H, s). [B] |
| 24 | 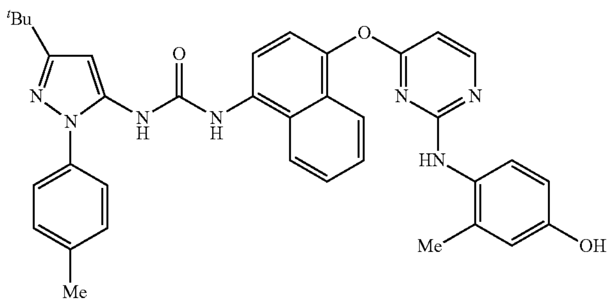 | 1-(3-(tert-butyl)-1-(p-tolyl)-1H-pyrazol-5-yl)-3-(4-((2-((4-hydroxy-2-methylphenyl)amino)pyrimidin-4-yl)oxy)naphthalen-1-yl)urea. R$^t$ 2.32 min (Method 2); m/z 614 (M + H)$^+$ (ES$^+$); $^1$H NMR ä: 1.28 (9H, s), 2.00 (3H, s), 2.39 (3H, s), 6.23 (1H, d), 6.38-6.39 (2H, overlapping m), 6.52 (1H, d), 6.78 (1H, d), 7.36-7.38 (3H, overlapping m), 7.46 (2H, d), 7.57 (1H, dt), 7.62 (1H, dt), 7.81 (1H, dd), 7.86 (1H, d), 8.05 (1H, d), 8.15 (1H, d), 8.47 (1H, s), 8.87 (1H, s), 9.12 (1H, s), 9.19 (1H, s). [B] |
| 25 | 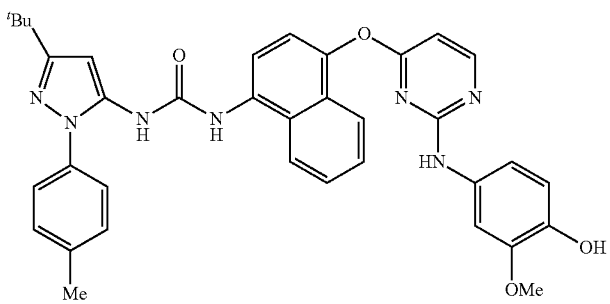 [SMILES: COc1cc(Nc2nccc(Oc3ccc(NC(=O)Nc4cc(C(C)(C)C)nn4-c4ccc(C)cc4)c4ccccc34)n2)ccc1O] | 1-(3-(tert-butyl)-1-(p-tolyl)-1H-pyrazol-5-yl)-3-(4-((2-((4-hydroxy-3-methoxyphenyl)amino)pyrimidin-4-yl)oxy)naphthalen-1-yl)urea. R$^t$ 2.43 min (Method 2); m/z 630 (M + H)$^+$ (ES$^+$): $^1$H NMR ä: 1.29 (9H, s), 2.40 (3H, s), 3.43 (3H, br s), 6.42 (2H, br s), 6.46 (1H, d), 6.75 (1H, br s), 7.04 (1H, br s), 7.37-7.39 (3H, overlapping m), 7.47 (2H, d), 7.56 (1H, dt), 7.62 (1H, dt), 7.81 (1H, dd), 7.92 (1H, d), 8.07 (1H, d), 8.32 (1H, d), 8.44 (1H, s), 8.83 (1H, s), 9.18 (1H, s), 9.20 (1H, br s). [B] |
| 26 | 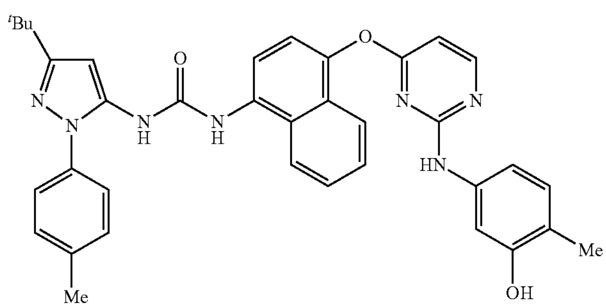 [SMILES: Cc1ccc(-n2nc(C(C)(C)C)cc2NC(=O)Nc2ccc(Oc3ccnc(Nc4ccc(C)c(O)c4)n3)c3ccccc23)cc1] | 1-(3-(tert-butyl)-1-(p-tolyl)-1H-pyrazol-5-yl)-3-(4-((2-((3-hydroxy-4-methylphenyl)amino)pyrimidin-4-yl)oxy)naphthalen-1-yl)urea. R$^t$ 2.59 min (Method 2); m/z 614 (M + H)$^+$ (ES$^+$): $^1$H NMR ä: 1.29 (9H, s), 1.97 (3H, s), 2.39 (3H, s), 6.41 (1H, s), 6.42 (1H. d), 6.70 (2H, br dd), 7.01 (1H, br s), 7.37-7.39 (3H, overlapping m), 7.47 (2H, d), 7.55 (1H, dt), 7.61 (1H, dt), 7.81 (1H, dd), 7.90 (1H, d), 8.07 (1H, d), 8.33 (1H, d), 8.88 (1H, s), 9.06 (1H, s), 9.22 (1H, s), 9.30 (1H, s). [B] |
| 27 | 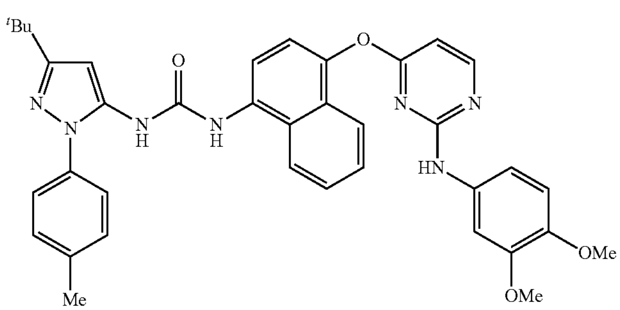 [SMILES: COc1ccc(Nc2nccc(Oc3ccc(NC(=O)Nc4cc(C(C)(C)C)nn4-c4ccc(C)cc4)c4ccccc34)n2)cc1OC] | 1-(3-(tert-butyl)-1-(p-tolyl)-1H-pyrazol-5-yl)-3-(4-((2-((3,4-dimethoxyphenyl)amino)pyrimidin-4-yl)oxy)naphthalen-1-yl)urea. R$^t$ 2.58 min (Method 2); m/z 644 (M + H)$^+$ (ES$^+$); $^1$H NMR ä: 1.29 (9H, s), 2.40 (3H, s), 3.44 (3H, s), 3.61 (3H, s), 6.40 (1H, s), 6.53 (1H, d), 6.61 (1H, d), 6.85 (1H, br s), 7.03 (1H, br s), 7.37-7.39 (3H, overlapping m), 7.47 (2H, d), 7.55 (1H, dt), 7.61 (1H, dt), 7.81 (1H, dd), 7.91 (1H, d), 8.07 (1H, d), 8.35 (1H, d), 8.80 (1H, s), 9.16 (1H, s), 9.29 (1H, s). [B] |

| Ex. No. | Structure | Name and Analytical Data [Route] |
|---|---|---|
| 28 | 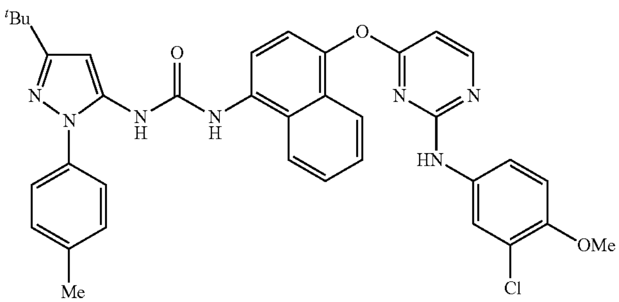 [SMILES: COc1ccc(Nc2nccc(Oc3ccc(NC(=O)Nc4cc(C(C)(C)C)nn4-c4ccc(C)cc4)c4ccccc34)n2)cc1Cl] | 1-(3-(tert-butyl)-1-(p-tolyl)-1H-pyrazol-5-yl)-3-(4-((2-((3-chloro-4-methoxyphenyl)amino)pyrimidin-4-yl)oxy)naphthalen-1-yl)urea.<br>R$^t$ 2.82 min (Method 2); m/z 648 (M + H)$^+$ (ES$^+$); $^1$H NMR ä: 1.29 (9H, s), 2.40 (3H, s), 3.70 (3H, s), 6.39 (1H, s), 6.60 (1H, d), 6.83 (1H, br d), 7.17 (1H, br s), 7.38-7.40 (4H, overlapping m), 7.47 (2H, d), 7.54 (1H, dt), 7.61 (1H, dt), 7.79 (1H, dd), 7.93 (1H, d), 8.07 (1H, d), 8.38 (1H, d), 8.86 (1H, s), 9.19 (1H, s), 9.51 (1H, s). [B] |
| 29 | 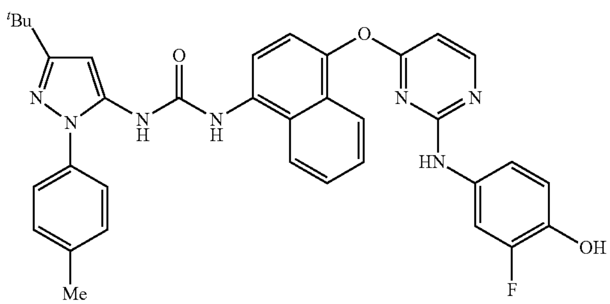 [SMILES: Cc1ccc(-n2nc(C(C)(C)C)cc2NC(=O)Nc2ccc(Oc3ccnc(Nc4ccc(O)c(F)c4)n3)c3ccccc23)cc1] | 1-(3-(tert-butyl)-1-(p-tolyl)-1H-pyrazol-5-yl)-3-(4-((2-((3-fluoro-4-hydroxyphenyl)amino)pyrimidin-4-yl)oxy)naphthalen-1-yl)urea.<br>R$^t$ 2.43 min (Method 2); m/z 618 (M + H)$^+$ (ES$^+$): $^1$H NMR ä: 1.29 (9H, s), 2.40 (3H, s), 6.42 (1H, s), 6.53 (1H, d), 6.61 (1H, br t), 6.89 (1H, br s), 7.18 (1H, br s), 7.37-7.39 (3H, overlapping m), 7.47 (2H, d), 7.55 (1H, dt), 7.61 (1H, dt), 7.78 (1H, dd), 7.95 (1H, d), 8.08 (1H, d), 8.35 (1H, d), 8.87 (1H, s), 9.19 (1H, s), 9.29 (1H, br s), 9.40 (1H, s). [B] |
| 30 | 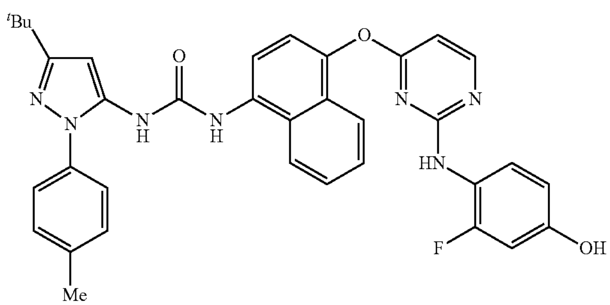 | 1-(3-(tert-butyl)-1-(p-tolyl)-1H-pyrazol-5-yl)-3-(4-((2-((2-fluoro-4-hydroxyphenyl)amino)pyrimidin-4-yl)oxy)naphthalen-1-yl)urea.<br>R$^t$ 2.49 min (Method 2); m/z 618 (M + H)$^+$ (ES$^+$); $^1$H NMR ä: 1.28 (9H, s), 2.39 (3H, s), 6.34 (1H, d), 6.38 (1H, br d), 6.41 (1H, s), 6.51 (1H, dd), 7.02 (1H, t), 7.36-7.38 (3H, overlapping m), 7.46 (2H, d), 7.57 (1H, dt), 7.62 (1H, dt), 7.80 (1H, dd), 7.89 (1H, d), 8.05 (1H, d), 8.20 (1H, d), 8.68 (1H, s), 8.77 (1H, s), 9.11 (1H, s), 9.63 (1H, s). [B] |
| 31 | 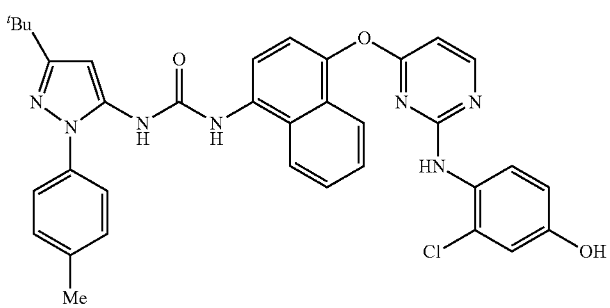 [SMILES: Cc1ccc(-n2nc(C(C)(C)C)cc2NC(=O)Nc2ccc(Oc3ccnc(Nc4ccc(O)cc4Cl)n3)c3ccccc23)cc1] | 1-(3-(tert-butyl)-1-(p-tolyl)-1H-pyrazol-5-yl)-3-(4-((2-((2-chloro-4-hydroxyphenyl)amino)pyrimidin-4-yl)oxy)naphthalen-1-yl)urea.<br>R$^t$ 2.67 min (Method 2); m/z 634 (M + H)$^+$ (ES$^+$): $^1$H NMR ä: 1.28 (9H, s), 2.39 (3H, s), 6.33 (1H, d), 6.41 (1H, s), 6.54 (1H, dd), 6.78 (1H, dd), 7.09 (1H, d), 7.36-7.38 (3H, overlapping m), 7.46 (2H, d), 7.57 (1H, dt), 7.63 (1H, dt), 7.80 (1H, dd), 7.89 (1H, d), 8.05 (1H, d), 8.20 (1H, d), 8.57 (1H, s), 8.78 (1H, s), 9.12 (1H, s), 9.69 (1H, s). [B] |
| 32 | 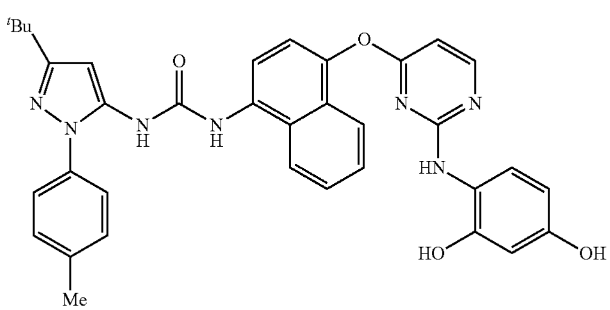 [SMILES: Cc1ccc(-n2nc(C(C)(C)C)cc2NC(=O)Nc2ccc(Oc3ccnc(Nc4ccc(O)cc4O)n3)c3ccccc23)cc1] | 1-(3-(tert-butyl)-1-(p-tolyl)-1H-pyrazol-5-yl)-3-(4-((2-((2,4-dihydroxyphenyl)amino)pyrimidin-4-yl)oxy)naphthalen-1-yl)urea.<br>R$^t$ 2.24 min (Method 2); m/z 616 (M + H)$^+$ (ES$^+$); 1H NMR ä: 1.29 (9H, s), 2.40 (3H, s), 5.92 (1H, br s), 6.25 (1H, d), 6.38 (1H, d), 6.42 (1H, s), 7.00 (1H, br s), 7.36-7.38 (3H, overlapping m), 7.47 (2H, d), 7.56 (1H, dt), 7.62 (1H, dt), 7.80 (1H, dd), 7.89 (1H, br s), 7.93 (1H, d), 8.07 (1H, d), 8.24 (1H, d), 8.84 (1H, s), 8.97 (1H, s), 9.18 (1H, s), 9.61 (1H, s). [B] |

| Ex. No. | Structure | Name and Analytical Data [Route] |
|---|---|---|
| 33 | (structure: 1-(3-(tert-butyl)-1-(4-methoxyphenyl)-1H-pyrazol-5-yl)-3-(4-((2-((4-hydroxyphenyl)amino)pyrimidin-4-yl)oxy)naphthalen-1-yl)urea) | 1-(3-(tert-butyl)-1-(4-methoxyphenyl)-1H-pyrazol-5-yl)-3-(4-((2-((4-hydroxyphenyl)amino)pyrimidin-4-yl)oxy)naphthalen-1-yl)urea. $R^t$ 2.31 min (Method 2); m/z 616 (M + H)$^+$ (ES$^+$); $^1$H NMR ä: 1.29 (9H, s), 3.84 (3H, s), 6.42-6.45 (4H, overlapping m), 7.08-7.11 (4H, overlapping m), 7.37 (1H, d), 7.50 (2H, d), 7.56 (1H, dt), 7.62 (1H, dt), 7.81 (1H, dd), 7.95 (1H, d), 8.08 (1H, d), 8.30 (1H, d), 8.77 (1H, s), 8.93 (1H, br s), 9.16 (1H, s), 9.19 (1H, br s). [A] |

Biological Testing: Experimental Methods

Enzyme Inhibition Assays

The kinase enzyme binding activities of compounds disclosed herein were determined using a proprietary assay which measures active site-directed competition binding to an immobilized ligand (Fabian, M. A. et al., *Nature Biotechnol.*, 2005, 23:329-336). These assays were conducted by DiscoverX (formerly Ambit; San Diego, Calif.). The Kd value (Dissociation constant value) was calculated as the index of affinity of the compounds to each kinase.

Enzyme Inhibition Assays

The enzyme inhibitory activities of compounds disclosed herein were determined by FRET using synthetic peptides labelled with both donor and acceptor fluorophores (Z-LYTE, Invitrogen Ltd., Paisley, UK).

p38 MAPKα Enzyme Inhibition

The inhibitory activities of test compounds against the p38 MAPKα isoform (MAPK14: Invitrogen), were evaluated indirectly by determining the level of activation/phosphorylation of the down-stream molecule, MAPKAP-K2. The p38 MAPKα protein (80 ng/mL, 2.5 μL) was mixed with the test compound (2.5 μL of either 4 μg/mL, 0.4 μg/mL, 0.04 μg/mL or 0.004 μg/mL) for 2 hr at RT. The mix solution (2.5 μL) of the p38a inactive target MAPKAP-K2 (Invitrogen, 600 ng/mL) and FRET peptide (8 μM; a phosphorylation target for MAPKAP-K2) was then added and the kinase reaction was initiated by adding ATP (40 μM, 2.5 μL). The mixture was incubated for 1 hr at RT. Development reagent (protease, 5 μL) was added for 1 hr prior to detection in a fluorescence microplate reader (Varioskan® Flash, ThermoFisher Scientific).

p38 MAPKγ Enzyme Inhibition

The inhibitory activities of compounds of the invention against p38MAPKγ (MAPK12: Invitrogen), were evaluated in a similar fashion to that described hereinabove. The enzyme (800 ng/mL, 2.5 μL) was incubated with the test compound (2.5 μL at either 4 μg/mL, 0.4 μg/mL, 0.04 μg/mL, or 0.004 μg/mL) for 2 hr at RT. The FRET peptides (8 μM, 2.5 μL), and appropriate ATP solution (2.5 μL, 400 μM) was then added to the enzymes/compound mixtures and incubated for 1 hr. Development reagent (protease, 5 μL) was added for 1 hr prior to detection in a fluorescence microplate reader (Varioskan® Flash, Thermo Scientific).

c-Src and Syk Enzyme Inhibition

The inhibitory activities of compounds of the invention against c-Src and Syk enzymes (Invitrogen), were evaluated in a similar fashion to that described hereinabove. The relevant enzyme (3000 ng/mL or 2000 ng/mL respectively, 2.5 μL) was incubated with the test compound (either 4 μg/mL, 0.4 μg/mL, 0.04 μg/mL, or 0.004 μg/mL, 2.5 μL each) for 2 hr at RT. The FRET peptides (8 μM, 2.5 μL), and appropriate ATP solutions (2.5 μL, 800 μM for c-Src, and 60 μM ATP for Syk) were then added to the enzyme/compound mixtures and incubated for 1 hr. Development reagent (protease, 5 μL) was added for 1 hr prior to detection in a fluorescence microplate reader (Varioskan® Flash, ThermoFisher Scientific).

GSK 3α Enzyme Inhibition

The inhibitory activities of test compounds against the GSK 3α enzyme isoform (Invitrogen), were evaluated by determining the level of activation/phosphorylation of the target peptide. The GSK3-α protein (500 ng/mL, 2.5 μL) was mixed with the test compound (2.5 μL at either 4 μg/mL, 0.4 μg/mL, 0.04 μg/mL, or 0.004 μg/mL) for 2 hr at RT. The FRET peptide (8 μM, 2.5 μL), which is a phosphorylation target for GSK3α, and ATP (40 μM, 2.5 μL) were then added to the enzyme/compound mixture and the resulting mixture incubated for 1 hr. Development reagent (protease, 5 μL) was added for 1 hr prior to detection in a fluorescence microplate reader (Varioskan® Flash, ThermoFisher Scientific).

In all cases, the site-specific protease cleaves non-phosphorylated peptide only and eliminates the FRET signal. Phosphorylation levels of each reaction were calculated using the ratio of coumarin emission (donor) over fluorescein emission (acceptor), for which low ratios indicate high phosphorylation and high ratios indicate low phosphorylation levels. The percentage inhibition of each reaction was calculated relative to non-inhibited control and the 50% inhibitory concentration ($IC_{50}$ value) was then calculated from the concentration-response curve.

Cellular Assays

LPS-induced TNFα/IL-8 Release in d-U937Cells

U937 cells, a human monocytic cell line, were differentiated into macrophage-type cells by incubation with PMA (100 ng/mL) for 48 to 72 hr. Cells were pre-incubated with final concentrations of test compound for 2 hr and were then stimulated with LPS (0.1 μg/mL; from *E. Coli:* 0111:B4, Sigma) for 4 hr. The supernatant was collected for determination of TNFα and IL-8 concentrations by sandwich ELISA (Duo-set, R&D systems). The inhibition of TNFα production was calculated as a percentage of that achieved by 10 μg/mL of BIRB796 at each concentration of test compound by comparison against vehicle control. The relative 50% effective concentration ($REC_{50}$) was determined from the resultant concentration-response curve. The inhibition of IL-8 production was calculated at each concentration of test compound by comparison with vehicle control.

The 50% inhibitory concentration ($IC_{50}$) was determined from the resultant concentration-response curve.

LPS-induced TNFα Release in THP-1 Cells

THP-1 cells, a human monocytic cell line, were stimulated with 3 μg/mL of LPS (from E. Coli; 0111:B4, Sigma) for 4 hr and the supernatant collected for determination of the TNFα concentration by sandwich ELISA (Duo-set, R&D systems). The inhibition of TNFα production was calculated at each concentration by comparison with vehicle control. The 50% inhibitory concentration ($IO_{50}$) was determined from the resultant concentration-response curve.

Poly I:C-induced ICAM-1 Expression in BEAS2B Cells

Poly I:C was used in these studies as a simple, RNA virus mimic. Poly I:C-Oligofectamine mixture (1 μg/mL Poly I:C, ±2% Oligofectamine, 25 μL; Invivogen Ltd., San Diego, Calif., and Invitrogen, Carlsbad, Calif., respectively) was transfected into BEAS2B cells (human bronchial epithelial cells, ATCC). Cells were pre-incubated with final concentrations of test compounds for 2 hr and the level of ICAM-1 expression on the cell surface was determined by cell-based ELISA. At a time point 18 hr after poly I:C transfection, cells were fixed with 4% formaldehyde in PBS (100 μL) and then endogenous peroxidase was quenched by the addition of washing buffer (100 μL, 0.05% Tween in PBS: PBS-Tween) containing 0.1% sodium azide and 1% hydrogen peroxide. Cells were washed with wash-buffer (3×200 μL). and after blocking the wells with 5% milk in PBS-Tween (100 μL) for 1 hr, the cells were incubated with anti-human ICAM-1 antibody (50 μL; Cell Signaling Technology, Danvers, Mass.) in 1% BSA PBS overnight at 4° C.

The cells were washed with PBS-Tween (3×200 μL) and incubated with the secondary antibody (100 μL; HRP-conjugated anti-rabbit IgG, Dako Ltd., Glostrup, Denmark). The cells were then incubated with of substrate (50 μL) for 2-20 min, followed by the addition of stop solution (50 μL, 1N $H_2SO_4$). The ICAM-1 signal was detected by reading and reading the absorbance at 450 nm against a reference wavelength of 655 nm using a spectrophotometer. The cells were then washed with PBS-Tween (3×200 μL) and total cell numbers in each well were determined by reading absorbance at 595 nm after Crystal Violet staining (50 μL of a 2% solution in PBS) and elution by 1% SDS solution (100 μL) in distilled water. The measured OD 450-655 readings were corrected for cell number by dividing with the OD595 reading in each well. The inhibition of ICAM-1 expression was calculated at each concentration of test compound by comparison with vehicle control. The 50% inhibitory concentration ($IC_{50}$) was determined from the resultant concentration-response curve.

Cell Mitosis Assay

Peripheral blood mononucleocytes (PBMCs) from healthy subjects were separated from whole blood (Quintiles, London, UK) using a density gradient (Histopaque®-1077, Sigma-Aldrich, Poole, UK). The PBMCs (3 million cells per sample) were subsequently treated with 2% PHA (Sigma-Aldrich, Poole, UK) for 48 hr, followed by a 20 hr exposure to varying concentrations of test compounds. At 2 hr before collection, PBMCs were treated with demecolcine (0.1 μg/mL; Invitrogen, Paisley, UK,) to arrest cells in metaphase. To observe mitotic cells, PBMCs were permeabilised and fixed by adding Intraprep (50 μL; Beckman Coulter, France), and stained with anti-phospho-histone 3 (0.26 ng/L; #9701; Cell Signalling, Danvers, Mass.) and propidium iodide (1 mg/mL; Sigma-Aldrich, Poole, UK,) as previously described (Muehlbauer P. A. and Schuler M. J., Mutation Research, 2003, 537:117-130). Fluorescence was observed using an ATTUNE flow cytometer (Invitrogen, Paisley, UK), gating for lymphocytes. The percentage inhibition of mitosis was calculated for each treatment relative to vehicle (0.5% DMSO) treatment.

Rhinovirus-Induced IL-8 Release and ICAM-1 Expression

Human rhinovirus RV16 was obtained from the American Type Culture Collection (Manassas, Va.). Viral stocks were generated by infecting Hela cells with HRV until 80% of the cells were cytopathic.

BEAS2B cells were infected with HRV at an MDI of 5 and incubated for 2 hr at 33° C. with gentle shaking for to promote absorption. The cells were then washed with PBS, fresh media added and the cells were incubated for a further 72 hr. The supernatant was collected for assay of IL-8 concentrations using a Duoset ELISA development kit (R&D systems, Minneapolis, Minn.).

The level of cell surface ICAM-1 expression was determined by cell-based ELISA. At 72 hr after infection, cells were fixed with 4% formaldehyde in PBS. After quenching endogenous peroxidase by adding 0.1% sodium azide and 1% hydrogen peroxide, wells were washed with wash-buffer (0.05% Tween in PBS: PBS-Tween). After blocking well with 5% milk in PBS-Tween for 1 hr, the cells were incubated with anti-human ICAM-1 antibody in 5% BSA PBS-Tween (1:500) overnight. Wells were washed with PBS-Tween and incubated with the secondary antibody (HRP-conjugated anti-rabbit IgG, Dako Ltd.). The ICAM-1 signal was detected by adding substrate and reading at 450 nm with a reference wavelength of 655 nm using a spectrophotometer. The wells were then washed with PBS-Tween and total cell numbers in each well were determined by reading absorbance at 595 nm after Crystal Violet staining and elution by 1% SDS solution. The measured $OD_{450-655}$ readings were corrected for cell number by dividing with the $OD_{595}$ reading in each well. Compounds were added 2 hr before HRV infection and 2 hr after infection when non-infected HRV was washed out.

Assessment of HRV16 Induced CPE in MRC5 Cells

MRC-5 cells were infected with HRV16 at an MOI of 1 in DMEM containing 5% FCS and 1.5 mM $MgCl_2$, followed by incubation for 1 hr at 33° C. to promote adsorption. The supernatants were aspirated, and then fresh media added followed by incubation for 4 days. Where appropriate, cells were pre-incubated with compound or DMSO for 2 hr, and the compounds and DMSO added again after washout of the virus.

Supernatants were aspirated and incubated with methylene blue solution (100 μL, 2% formaldehyde, 10% methanol and 0.175% Methylene Blue) for 2 hr at RT. After washing, 1% SDS in distilled water (100 μL) was added to each well, and the plates were shaken lightly for 1-2 hr prior to reading the absorbance at 660 nm. The percentage inhibition for each well was calculated. The $IC_{50}$ value was calculated from the concentration-response curve generated by the serial dilutions of the test compounds.

In Vitro RSV Virus Load in Primary Bronchial Epithelial Cells.

Normal human bronchial epithelial cells (NHBEC) grown in 96 well plates were infected with RSV A2 (Strain A2, HPA, Salisbury, UK) at an MOI of 0.001 in the LHC8 Media:RPMI-1640 (50:50) containing 15 mM magnesium chloride and incubated for 1 hr at 37° C. for adsorption. The cells were then washed with PBS (3×200 μL), fresh media (200 μL) was added and incubation continued for 4 days. Where appropriate, cells were pre-incubated with the compound or DMSO for 2 hr, and then added again after washout of the virus.

The cells were fixed with 4% formaldehyde in PBS solution (50 µL) for 20 min, washed with washing buffer (3×200 µL; PBS including 0.5% BSA and 0.05% Tween-20) and incubated with blocking solution (5% condensed milk in PBS) for 1 hr. Cells were then washed with washing buffer (3×200 µL) and incubated for 1 hr at RT with anti-RSV (2F7) F-fusion protein antibody (40 µL; mouse monoclonal, lot 798760, Cat. No. ab43812, Abcam) in 5% BSA in PBS-tween). After washing, cells were incubated with an HRP-conjugated secondary antibody solution (50 µL) in 5% BSA in PBS-Tween (lot 00053170, Cat. No. PO447, Dako) and then TMB substrate (50 µL; substrate reagent pack, lot 269472, Cat. No. DY999, R&D Systems, Inc.) was added. This reaction was stopped by the addition of 2N $H_2SO_4$ (50 µL) and the resultant signal was determined colorimetrically (OD: 450 nm with a reference wavelength of 655 nm) in a microplate reader (Varioskan® Flash, ThermoFisher Scientific).

Cells were then washed and a 2.5% crystal violet solution (50 µL; lot 8656, Cat. No. PL7000, Pro-Lab Diagnostics) was applied for 30 min. After washing with washing buffer, 1% SDS in distilled water (100 µL) was added to each well, and plates were shaken lightly on the shaker for 1 hr prior to reading the absorbance at 595 nm. The measured $OD_{450-655}$ readings were corrected to the cell number by dividing the $OD_{450-655}$ by the $OD_{595}$ readings. The percentage inhibition for each well was calculated and the $IC_{50}$ value was calculated from the concentration-response curve generated from the serial dilutions of compound.

The Effect of Test Compounds on Cell Viability: MTT Assay

Differentiated U937 cells were pre-incubated with each test compound (final concentration 1 µg/mL or 10 µg/mL in 200 µL media indicated below) under two protocols: the first for 4 hr in 5% FCS RPMI1640 media and the second in 10% FCS RPMI1640 media for 24 h. The supernatant was replaced with new media (200 µL) and MTT stock solution (10 µL, 5 mg/mL) was added to each well. After incubation for 1 hr the media were removed, DMSO (200 µL) was added to each well and the plates were shaken lightly for 1 hr prior to reading the absorbance at 550 nm. The percentage loss of cell viability was calculated for each well relative to vehicle (0.5% DMSO) treatment. Consequently an apparent increase in cell viability for drug treatment relative to vehicle is tabulated as a negative percentage.

Cytokine Production in Sputum Macrophages from COPD.

Patients with COPD were inhaled with a nebulised solution of 3% (w/v) hypertonic saline using an ultrasonic nebuliser (Devilbiss, Carthage, Mo.) with tidal breathing for 5 min. This procedure was repeated a maximum of three times until enough sputum was obtained. The sputum samples were homogenized and mixed vigorously using a vortex mixer in 0.02% v/v dithiothreitol (DTT) solution. The samples were re-suspended in PBS (40 mL) followed by centrifugation at 1500 rpm at 4° C. for 10 min to obtain sputum cell pellets. The pellets were washed twice with PBS (40 mL). The sputum cells were then re-suspended in macrophage serum-free medium (macrophage-SFM, Life technologies, Paisley, UK; to achieve $2×10^6$/well in a 24 well plate) containing 20 U/mL penicillin, 0.02 mg/mL streptomycin and 5 µg/mL amphotericin B and seeded on high bound 96-well plate, followed by incubation for 2 hr at 37° C. and at 5% $CO_2$ to allow the macrophages to attach to the bottom of the plate. The cells on the plate were washed with fresh macrophage-SFM (200 µL/well) to remove neutrophils and other contaminated cells. The adherent cells (mainly sputum macrophages) on the plate were used for further analysis. Sputum induction and isolation were conducted in Quintiles Drug Research Unit at Guys Hospital and ethics approval and written informed consent was obtained by Quintiles.

Where appropriate, 1 µL of a solution containing either the test compound or reference article at the stated concentrations or alternatively 1 µL of DMSO as the vehicle control was added to each well (200 µL in media) and the cells were incubated for 2 hr. The cells were stimulated with LPS solution (50 µL, final concentration: 1 µg/mL) and incubated for 4 hr at 37° C. and 5% $CO_2$. The supernatant was then collected and kept at −80° C. Millipore's luminex kits were used to measure the four analytes. After thawing the supernatant, the magnetic antibody beads were multiplexed and incubated in a 96-well plate with standard, background solution or the appropriate volume of sample overnight with shaking at 4° C. After washing twice with 200 µL of wash buffer provided by the kit per well using a magnetic plate washer, the beads were incubated for 1 hr at RT with 25 µL of the biotin conjugated antibody solution provided by the kit with shaking. Streptavidin solution was added for 30 min with shaking at RT. After washing with 200 uL wash buffer per well, the beads were resuspended in sheath fluid (150 µL) and analyzed immediately. The level of each analyte in the supernatant was calculated using Xcel Fit software with a 4 or 5-parameter equation using each standard curve. The inhibitions of each cytokine production were calculated at each concentration by comparison with vehicle control. The $IC_{50}$ values were determined from concentration-inhibition curves using XL-Fit (idbs, Guildford, UK)

Cytokine Production in Primary Bronchial Epithelial Cells from COPD.

Primary airway epithelial cells obtained from patients with COPD were purchased from Asterand (Royston, UK), and maintained in bronchial epithelial cell growth media that was prepared by mixing together LHC8 (Invitrogen) (500 mL), with LHC9 (Invitrogen) (500 mL) and 3 µL of retinoic acid solution (5 mg/mL in neat DMSO. The media was removed by aspiration and fresh BEGM (200 µL) was added to each well. Where appropriate, 1 µL of a solution of the test compound at the state concentrations or 1 µL of DMSO as the vehicle control was added and the cells were incubated for 2 hr. The cells were stimulated with TNFα (50 µL; final concentration 50 ng/mL) and then incubated for 4 hr at 37° C. and 5% $CO_2$. The supernatant was then collected and kept at −20° C.

The levels of IL-6 and IL-8 were determined by ELISA using R&D Systems' Human IL-6 and IL-8 Duoset® Elisa Kits. The inhibition of IL-6 and IL-8 production was calculated at each concentration by comparison with vehicle control. The 50% inhibitory concentrations ($IC_{50}$) were determined from the resultant concentration-response curves using XL-Fit (idbs, Guildford, UK).

In Vivo Screening: Pharmacodynamics and Anti-Inflammatory Activity

LPS-Induced Neutrophil Accumulation in Mice

Non-fasted Balb/c mice were dosed by the intra tracheal route with either vehicle, or the test substance at the indicated times (within the range 2-8 hr) before stimulation of the inflammatory response by application of an LPS challenge. At T=0, mice were placed into an exposure chamber and exposed to LPS (7.0 mL, 0.5 mg/mL solution in PBS) for 30 min). After a further 8 hr the animals were anesthetized, their tracheas cannulated and BALF extracted by infusing and then withdrawing from their lungs 1.0 mL of PBS via the tracheal catheter. Total and differential white cell counts in the BALF samples were measured using a Neubaur haemocytometer. Cytospin smears of the BALF samples were prepared by centrifugation at 200 rpm for 5 min at RT and stained using a DiffQuik stain system (Dade Behring). Cells were counted using oil immersion microscopy. Data for neutrophil numbers in BAL are shown as mean±S.E.M. (standard error of the mean). The percentage inhibition of neutrophil accumulation was calculated for each treatment relative to vehicle treatment.

Cigarette Smoke Model

NJ mice (males, 5 weeks old) were exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances were administered intra-nasally (35 μL of solution in 50% DMSO/PBS) once daily for 3 days after the final cigarette smoke exposure. At 12 hr after the last dosing, each of the animals was anesthetized, the trachea cannulated and bronchoalveolar lavage fluid (BALF) was collected. The numbers of alveolar macrophages and neutrophils were determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil). BALF was centrifuged and the supernatant was collected. The level of keratinocyte chemoattractant (KC; CXCL1) in BALF was quantitated using a Quentikine® mouse KC ELISA kit (R&D systems, Inc., Minneapolis, Minn., USA).

Summary of In Vitro and In Vivo Screening Results

The in vitro profile of the compounds of the present invention disclosed herein, as determined using the protocols described above, are presented below (Tables 3a-h) in comparison with a structurally related Reference Compound which is N-(4-(4-(3-(3-tert-butyl-1-p-tolyl-1H-pyrazol-5-yl)ureido)naphthalen-1-yloxy)pyridin-2-yl)-2-methoxyacetamide, which has been previously described as a potent anti-inflammatory agent with anti-viral activity (Ito, K. et al., WO 2010/112936, PCT/GB2010/050575. 7 Oct. 2010 and Ito, K. et al., WO 2010/067130, PCT/GB2009/051702, 17 Jun. 2010.

The compounds of the present invention demonstrate a very similar inhibitory profile to the Reference Compound in the range of kinase enzyme assays with the marked exception of the inhibition the molecule possess against of the enzyme GSK3α, which is very much weaker than the Reference Compound (Table 3a and Table 3b).

TABLE 3a p38 MAPK and GSK3α Enzyme Profile of Compound Examples

| Test Compound Example No. | IC50 Values for Enzyme Inhibition (nM) | | |
|---|---|---|---|
| | p38 MAPKα | p38 MAPKγ | GSK3α |
| Reference Compound | 12 | 344 | 45 |
| 1 | 60 | 3739 | >17000 |
| 2 | 164 | 557 | >1670 |
| 3 | 173 | 1503 | 2494 |
| 4 | 165 | 8198 | >16600 |
| 5 | 161 | >16300 | >16300 |
| 6 | 161 | >16200 | >16200 |
| 7 | 170 | 1702 | 3505 |
| 8 | 151 | >15500 | >15500 |
| 9 | 171 | 760 | 3260 |
| 10 | 195 | >16300 | >16300 |
| 11 | 356 | >16730 | >16700 |
| 12 | 169 | >16700 | >16730 |
| 13 | 262 | >16200 | >16200 |
| 14 | 119 | >16300 | >16300 |
| 15 | 155 | >16600 | >16600 |
| 16 | 616 | >16200 | >16200 |

TABLE 3a-continued p38 MAPK and GSK3α Enzyme Profile of Compound Examples

| Test Compound Example No. | IC50 Values for Enzyme Inhibition (nM) | | |
|---|---|---|---|
| | p38 MAPKα | p38 MAPKγ | GSK3α |
| 17 | 83 | >16300 | >16300 |
| 18 | 133 | >15800 | >15800 |
| 19 | 98 | >15100 | >15100 |
| 20 | 9 | >16000 | >16000 |
| 21 | 33 | >1670 | >1670 |
| 22 | 281 | >1590 | >1590 |
| 23 | 212 | >1660 | >1660 |
| 24 | 36 | 695 | >1590 |
| 25 | 77 | 281 | >1590 |
| 26 | 549 | >1630 | >1630 |
| 27 | 105 | 535 | 2108 |
| 28 | 1422 | >1540 | >1540 |
| 29 | 311 | 423 | >1620 |
| 30 | 68 | >1620 | >1620 |
| 31 | 118 | >1580 | >1580 |
| 32 | 189 | >1620 | >1620 |
| 33 | 60 | 264 | 2377 |

TABLE 3b c-Src and Syk Enzyme Profile of Compound (I)

| Test Compound | $IC_{50}$ Values for Enzyme Inhibition (nM) | |
|---|---|---|
| | c-Src | Syk |
| Example 1 | 22 | 334 |
| Reference Compound | 5 | 42 |

The kinase binding profile of Example 1 of the present invention was also compared with the Reference Compound against p38 MAPK, HCK, cSrc, Syk, and GSK3α/β. Example 1 displayed a very different phenotype, demonstrating profound inhibition of binding versus p38MAPK, HCK, cSrc and Syk kinases, without significant effect against GSK3α (Table 3c).

TABLE 3c

Comparison of the Enzyme Binding Profile of Compound (I) with the Reference Compound.

| Test Compound | Kd value for kinase binding (nM) | | | | | | |
|---|---|---|---|---|---|---|---|
| | p38 MAPKα | p38 MAPKγ | HCK | cSrc | Syk | GSK3α | GSK3β |
| Example 1 | 20 | 43 | 8 | 10 | 14 | 20000 | 1200 |
| Reference compound | 1 | 5 | 5 | 4 | 9 | 180 | 24 |

The compounds of the present invention demonstrate a similar profile to the Reference Compound in cellular assays that reveal anti-inflammatory properties against endotoxin mediated release of both TNFα and IL-8 (Table 3d). The profiles of the compounds are also similar in cellular systems measuring their effects on respiratory virus replication (HRV induced ICAM1 and CPE expression and RSV stimulated expression of F-protein) as well as virus-induced inflammation (HRV evoked release of IL-8) (Table 3e and Table 3f).

TABLE 3d

Inhibition of LPS induced TNFα and IL-8 Release and PolyIC induced ICAM-1 Expression for Compound Examples

| Test Compound Example No. | LPS Induced Release (nM) TNFα $IC_{50}$ (THP1) | LPS Induced Release (nM) TNFα $REC_{50}$ (dU937) | LPS Induced Release (nM) IL-8 $IC_{50}$ (dU937) | PolyIC/ ICAM1 (nM) $IC_{50}$ (BEAS2B) |
|---|---|---|---|---|
| Reference Compound | 13 | 0.13 | 1.3 | 2.1 |
| 1 | 3.4 | 2.3 | 2.2 | 10 |
| 2 | 2.8 | 2.4 | 2.7 | 4.3 |
| 3 | 1.2 | 1.7 | 1.8 | 4.1 |
| 4 | 4.6 | 3.1 | 2.3 | 144 |
| 5 | 66 | 2.9 | 6.2 | 17 |
| 6 | 225 | 7.0 | 15 | 56 |
| 7 | 10 | 1.7 | 2.1 | 23 |
| 8 | 225 | 227 | 235 | 22 |
| 9 | 1.3 | 1.7 | 2.2 | 3.0 |
| 10 | 45 | 15 | 15 | 43 |
| 11 | 21 | 35 | >1675 | 11 |
| 12 | 30 | 2.0 | 2.4 | 2.7 |
| 13 | 1603 | >1618 | >1618 | 3.0 |
| 14 | 2.7 | 2.0 | 1.6 | 9.8 |
| 15 | 3.0 | 2.2 | 2.3 | 9.3 |
| 16 | 4.1 | 1.1 | 0.31 | 36 |
| 17 | 4.3 | 2.0 | 2.1 | 6.7 |
| 18 | 157 | 13 | 15 | 28 |
| 19 | 192 | 13 | 14 | 43 |
| 20 | 121 | 18 | 23 | 16 |
| 21 | 17. | 9.7 | >1677 | 36 |
| 22 | 30 | 17 | >1592 | 13 |
| 23 | 24 | 8.0 | 22 | 4.2 |
| 24 | 0.8 | 2.3 | 86 | 5.0 |
| 25 | 0.4 | 0.84 | 1.5 | 2.5 |
| 26 | 1.9 | 4.1 | 6.6 | 8.4 |
| 27 | 0.5 | 0.54 | 2.0 | 1.6 |
| 28 | 0.4 | 14 | 18 | 3.0 |
| 29 | 1.6 | 11 | 2.3 | 2.8 |
| 30 | 1.6 | 1 | 3.0 | 11 |
| 31 | 6.1 | 16 | 32 | 80 |
| 32 | 14 | 12 | 9.7 | 21 |
| 33 | 0.5 | 7.4 | 6.3 | 2.6 |

TABLE 3e

The Effect of Compound Examples on HRV-16 propagation (expression of ICAM-1 and CPE) and Inflammation (IL-8 release) and on RSV propagation (F-protein expression).

| Test Compound Example No. | $IC_{50}$ Values (nM) and/or % inhibition at 0.04 μg/mL HRV IL-8 (BEAS2B) | HRV CPE (MRC5) | RSV (F-Elisa) (HBEC) |
|---|---|---|---|
| Reference Compound | 0.065 | 4.7 | 22.0 |
| 1 | 0.036 | 17.1 (57%) | 15.4 (85%) |
| 2 | 100% | 5% | 42% |
| 3 | 100% | 100% | NT |
| 4 | 100% | 44% | NT |
| 5 | 49% | 91% | NT |
| 6 | 77% | 46% | NT |
| 7 | 100% | NE | NT |
| 8 | 100% | 100% | NT |
| 9 | 100% | 100% | NT |
| 10 | 100% | 100% | NT |
| 11 | 100% | 100% | NT |
| 12 | 100% | 100% | NT |
| 13 | 100% | 100% | NT |
| 14 | 100% | 100% | NT |
| 15 | 100% | 100% | NT |
| 16 | 100% | 10% | NT |
| 17 | 100% | NE | NT |
| 18 | 100% | NE | NT |
| 19 | 100% | NE | NT |
| 20 | 100% | NE | NT |
| 21 | 100% | 3% | 66% |
| 22 | 100% | 48% | 78% |
| 23 | 100% | 18% | 41% |
| 24 | 100% | 41% | NT |
| 25 | 100% | 33%* | NT |
| 26 | 100% | 69% | NT |
| 27 | 100% | 51% | NT |
| 28 | 100% | 54% | NT |
| 29 | 100% | 13% | NT |
| 30 | 100% | NE | NT |
| 31 | 100% | NE | NT |
| 32 | 100% | 26% | NT |
| 33 | 100% | 44% | NT |

NE: no effect, ≤0% at 0.04 μg/mL;
*tested at 0.0008 μg/mL, low cell viability at 0.04 μg/mL;
NT: not tested

TABLE 3f

The Effect of Example 1 on Inflammation (Expression of ICAM-1)

| Test Substance | $IC_{50}$ Values (nM) for HRV Stimulated Release/Expression ICAM1 (BEAS2B) |
|---|---|
| Example 1 | 0.023 |
| Reference Compound | 0.37 |

Example 1 of the present invention demonstrated higher efficacy in pro-inflammatory cytokine production in sputum macrophage and bronchial epithelial cells obtained from COPD patients, which were largely insensitive to fluticasone propionate, a corticosteroid, (Table 3g).

TABLE 3g

The Effect of Example 1 and Fluticasone propionate on pro-inflammatory cytokine release in sputum macrophages and bronchial epithelial cell from COPD patients.

| Cells Type | Cytokine | $IC_{50}$ values (nM) and/or E max (% in parentheses)[1] Example 1 | Fluticasone Propionate |
|---|---|---|---|
| Sputum Macrophage | IL-6 | 43 (79) | (26) |
| | IL-8 | 68 (64) | (19) |
| | TNFα | 17 (86) | (18) |
| | MIP1α | 7.5 (89) | (20) |
| Bronchial Epithelial Cell | IL-6 | 1.7 (100) | (38) |
| | IL-8 | 0.85 (100) | (17) |

[1]E-max values (maximum inhibiton) were calculated as the % inhibition obtained at 0.1 μg/mL However, advantageously, the compounds of the present invention show markedly less activity in assay systems that measure its impact on cell viability and cell division (mitosis) indicating that the compound is likely to possess a superior therapeutic index over the Reference Compound (Table 3h).

TABLE 3h

Effect of Compound Examples on Cellular Viability and Cell Division

| Test Compound | MTT Assay [1] Cell viability at time point in d-U937 Cells | | Mitosis Assay % inhibition in PBMC Cells at concn | |
|---|---|---|---|---|
| Example No. | 4 h | 24 h | 1 μg/mL | 5 μg/mL |
| Reference Compound | −ve | +ve | NT | 87.8 |
| 1 | −ve | −ve | 13.7 | 31.3 |
| 2 | −ve | −ve | NT | 70.6 |
| 3 | −ve | −ve | NT | NT |
| 4 | −ve | −ve | NT | NT |
| 5 | −ve | −ve | NT | NT |
| 6 | −ve | −ve | NT | NT |
| 7 | −ve | −ve | NT | 10.2 |
| 8 | −ve | −ve | 15.6 | NT |
| 9 | −ve | −ve | NT | 50.3 |
| 10 | −ve | −ve | NT | NT |
| 11 | −ve | −ve | NT | NT |
| 12 | −ve | −ve | NT | NT |
| 13 | −ve | −ve | NT | NT |
| 14 | −ve | −ve | NT | NT |
| 15 | −ve | −ve | NT | NT |
| 16 | −ve | −ve | NT | NT |
| 17 | −ve | −ve | NT | NT |
| 18 | −ve | −ve | NT | NT |
| 19 | −ve | −ve | n.t. | NT |
| 20 | −ve | −ve | NT | NT |
| 21 | −ve | −ve | NT | NT |
| 22 | −ve | −ve | NT | 70.8 |
| 23 | −ve | −ve | NT | NT |
| 24 | −ve | −ve | NT | NT |
| 25 | −ve | −ve | 29.1 | 63.5 |
| 26 | −ve | −ve | NT | NT |
| 27 | +ve | −ve | NT | 11.2 |
| 28 | −ve | −ve | NT | NT |
| 29 | +ve | −ve | NT | NT |
| 30 | −ve | −ve | NT | NT |
| 31 | −ve | −ve | NT | NT |
| 32 | −ve | −ve | NT | 33.0 |
| 33 | −ve | −ve | NT | 67.2 |

[1] Cell viability screen: −ve and +ve indicate the value is below and above respectively, the no significant effect threshold defined as 30% inhibition at 1 μg/mL at the time point indicated;
NT: not tested Treatment of mice with Example 1 was found to produce a dose dependent inhibition on LPS-induced neutrophil accumulation and a time course experiment revealed that the drug substance had a long duration of action (Table 4).

TABLE 4

The Effects of Treatment with Example 1 on LPS-Induced Airway Neutrophilia in Mice.

| Example 1 | Neutrophil numbers in BALF (×$10^5$/mL) at pre-dose time indicated (% inhibition)[1] | | |
|---|---|---|---|
| (mg/mL) | 2 hr | 8 hr | 12 hr |
| Vehicle | 18.9 ± 2.5 | — | — |
| 0.05 | 15.6 ± 2.1 (18) | — | — |
| 0.2 | 9.8 ± 1.6 (48) | — | — |
| 1.0 | 4.4 ± 0.89 (77) | 9.9 ± 1.8 (48) | 18.3 ± 2.3 (4) |

[1] N = 8 per group

The result of treatment with Example 1 on macrophage and neutrophil accumulation in BALF in the mouse cigarette smoke model was investigated (Table 5). The cigarette smoke model used for this study is reported to be a corticosteroid refractory system, (Medicherla S. et al., *J. Pharmacol. Exp. Ther.*, 2008, 324(3):921-9.) and it was confirmed that fluticasone propionate did not inhibit either neutrophil or macrophage accumulation into airways at 1.75 μg/mouse (35 μL, bid, i.n.), the same dose that produced >80% inhibition of LPS-induced neutrophil accumulation.

Treatment of mice with Example 1 was found to produce a dose-dependent inhibition on both macrophage and neutrophil accumulation in BALF induced by cigarette smoke.

TABLE 5

The Effects of Treatment with Example 1 on Tobacco Smoke in Mice.

| Treatment | Cell numbers in BALF ×$10^4$/mL (% inhibition) | |
|---|---|---|
| Example 1 (μg/mL) | Macrophage | Neutrophil |
| Vehicle + Air | 4.3 ± 0.45 | 2.6 ± 0.21 |
| Vehicle + Tobacco Smoke | 14.4 ± 0.33 | 13.7 ± 0.31 |
| 0.32 | 13.3 ± 0.20 (11) | 12.4 ± 0.32 (12) |
| 1.6 | 11.6 ± 0.42 (28) | 10.5 ± 0.06 (29) |
| 8.0 | 10.1 ± 0.42 (43) | 9.1 ± 0.28 (41) |
| 40 | 7.9 ± 0.20 (64) | 7.9 ± 0.34 (52) |

The data for cell numbers are shown as the mean ± SEM, N = 5

Treatment of mice with Example 1 also inhibited cigarette smoke induced CXCL1 (KC) production in BALF in a dose-dependent manner (Table 6).

TABLE 6

The Effects of Treatment with Example 1 on CXCL1 (KC) release in BALF on Tobacco Smoke in Mice.

| Treatment Example 1 (μg/mL) | CXCL1 in BALF pg/mL (% inhibition) |
|---|---|
| Vehicle + Air | 8.2 ± 0.30 |
| Vehicle + Tobacco Smoke | 13.6 ± 1.69 |
| 0.32 | 13.6 ± 1.69 (0) |
| 1.6 | 12.2 ± 0.96 (26) |
| 8.0 | 11.4 ± 0.15 (41) |
| 40 | 9.5 ± 0.84 (76) |

The data for CXCL level are shown as the mean ± SEM, N = 5

In summary, these results suggest that compounds of the present invention have similar anti-inflammatory properties to the Reference Compound disclosed supra and, advantageously, are associated with a higher therapeutic index.

Formulation Example

Preparation of Pharmaceutical Formulations

An exemplary pharmaceutical formulation of the invention would consist of 0.4 wt. % of Example 1 (as the anhydrous free base in solid crystalline form), 98.6 wt. % lactose monohydrate (inhalation grade) and 1.0 wt. % magnesium stearate, wherein the wt. % of all components is based on the weight of the dry pharmaceutical formulation.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:
1. A compound of formula (I)

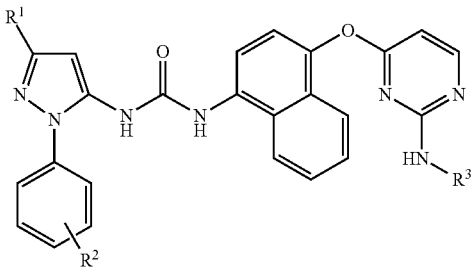

wherein:
R¹ is selected from the group consisting of $C_{1-10}$ alkyl, $C_{3-10}$ cycloalkyl and halo substituted $C_{1-10}$ alkyl,
R² is selected from the group consisting of hydrogen, hydroxyl, halogen, $C_{1-6}$ alkyl and $C_{1-6}$ alkoxy,
R³ represents phenyl optionally substituted by 1 to 3 substituents independently selected from the group consisting of hydroxyl, halogen, $C_{1-6}$ alkyl, and $C_{1-6}$ alkoxy,
or a pharmaceutically acceptable salt thereof and stereoisomers and tautomers thereof.

2. A compound according to claim 1, wherein R¹ represents t-butyl.

3. A compound according to claim 2, wherein R² is a meta or para substituent.

4. A compound according to claim 3, wherein R² is selected from the group consisting of hydrogen, methyl, methoxy and hydroxyl.

5. A compound according to claim 4, wherein R³ represents unsubstituted phenyl.

6. A compound according to claim 4, wherein R³ represents phenyl optionally substituted with one to three substituents independently selected from the group consisting of methyl, ethyl, isopropyl, hydroxyl, methoxy, fluoro and chloro.

7. A compound according to claim 6, wherein R³ is substituted at the para position with a substituent selected from the group consisting of hydrogen, methyl, hydroxyl, methoxy, fluoro and chloro.

8. A compound according to claim 1 selected from the group consisting of:
  1-(3-(tert-Butyl)-1-(p-tolyl)-1H-pyrazol-5-yl)-3-(4-(2-(phenylamino)pyrimidin-4-yloxy)naphthalen-1-yl) urea;
  1-(3-(tert-Butyl)-1-(p-tolyl)-1H-pyrazol-5-yl)-3-(4-((2-(3-hydroxyphenyl) amino)pyrimidin-4-yl)oxy)naphthalen-1-yl)urea;
  1-(3-(tert-butyl)-1-(4-hydroxyphenyl)-1H-pyrazol-5-yl)-3-(4-((2-(phenylamino) pyrimidin-4-yl)oxy)naphthalen-1-yl)urea;
  1-(3-(tert-butyl)-1-(p-tolyl)-1H-pyrazol-5-yl)-3-(4-((2-(2-fluorophenyl)amino)pyrimidin-4-yl)oxy)naphthalen-1-yl)urea;
  1-(3-(tert-butyl)-1-(p-tolyl)-1H-pyrazol-5-yl)-3-(4-((2-((2-methoxyphenyl)amino) pyrimidin-4-yl)oxy)naphthalen-1-yl)urea;
  1-(3-(tert-butyl)-1-(p-tolyl)-1H-pyrazol-5-yl)-3-(4-((2-((2-chlorophenyl)amino)pyrimidin-4-yl)oxy)naphthalen-1-yl)urea;
  1-(3-(tert-butyl)-1-(4-methoxyphenyl)-1H-pyrazol-5-yl)-3-(4-((2-(phenylamino) pyrimidin-4-yl)oxy)naphthalen-1-yl)urea;
  1-(3-(tert-butyl)-1-(p-tolyl)-1H-pyrazol-5-yl)-3-(4-((2-((2,4-dimethoxyphenyl)amino) pyrimidin-4-yl)oxy)naphthalen-1-yl)urea;
  1-(3-(tert-butyl)-1-(p-tolyl)-1H-pyrazol-5-yl)-3-(4-((2-((4-hydroxyphenyl)amino) pyrimidin-4-yl)oxy)naphthalen-1-yl)urea;
  1-(3-(tert-butyl)-1-(p-tolyl)-1H-pyrazol-5-yl)-3-(4-((2-((2,5-dimethylphenyl)amino) pyrimidin-4-yl)oxy)naphthalen-1-yl)urea;
  1-(3-(tert-butyl)-1-(p-tolyl)-1H-pyrazol-5-yl)-3-(4-((2-(p-tolylamino)pyrimidin-4-yl)oxy) naphthalen-1-yl)urea;
  1-(3-(tert-butyl)-1-(p-tolyl)-1H-pyrazol-5-yl)-3-(4-((2-(m-tolylamino)pyrimidin-4-yl)oxy) naphthalen-1-yl)urea;
  1-(3-(tert-butyl)-1-(p-tolyl)-1H-pyrazol-5-yl)-3-(4-((2-(3-chlorophenyl)amino)pyrimidin-4-yl)oxy)naphthalen-1-yl)urea;
  1-(3-(tert-butyl)-1-(p-tolyl)-1H-pyrazol-5-yl)-3-(4-((2-((3-methoxyphenyl)amino) pyrimidin-4-yl)oxy)naphthalen-1-yl)urea;
  1-(3-(tert-butyl)-1-(p-tolyl)-1H-pyrazol-5-yl)-3-(4-((2-((3-fluorophenyl)amino)pyrimidin-4-yl)oxy)naphthalen-1-yl)urea;
  1-(3-(tert-butyl)-1-(p-tolyl)-1H-pyrazol-5-yl)-3-(4-((2-((4-chlorophenyl)amino)pyrimidin-4-yl)oxy)naphthalen-1-yl)urea;
  1-(3-(tert-butyl)-1-(p-tolyl)-1H-pyrazol-5-yl)-3-(4-((2-((4-methoxyphenyl)amino) pyrimidin-4-yl)oxy)naphthalen-1-yl)urea;
  1-(3-(tert-butyl)-1-(p-tolyl)-1H-pyrazol-5-yl)-3-(4-((2-((4-chloro-2-methylphenyl)amino) pyrimidin-4-yl)oxy)naphthalen-1-yl)urea;
  1-(3-(tert-butyl)-1-(p-tolyl)-1H-pyrazol-5-yl)-3-(4-((2-((2-chlorophenyl)amino)pyrimidin-4-yl)oxy)naphthalen-1-yl)urea;
  1-(3-(tert-butyl)-1-(p-tolyl)-1H-pyrazol-5-yl)-3-(4-((2-((2-isopropylphenyl)amino) pyrimidin-4-yl)oxy)naphthalen-1-yl)urea;
  1-(3-(tert-butyl)-1-(p-tolyl)-1H-pyrazol-5-yl)-3-(4-((2-(o-tolylamino)pyrimidin-4-yl)oxy) naphthalen-1-yl)urea;
  1-(3-(tert-butyl)-1-(p-tolyl)-1H-pyrazol-5-yl)-3-(4-((2-((4-ethoxyphenyl)amino)pyrimidin-4-yl)oxy)naphthalen-1-yl)urea;
  1-(3-(tert-butyl)-1-(p-tolyl)-1H-pyrazol-5-yl)-3-(4-((2-((4-fluorophenyl)amino)pyrimidin-4-yl)oxy)naphthalen-1-yl)urea;
  1-(3-(tert-butyl)-1-(p-tolyl)-1H-pyrazol-5-yl)-3-(4-((2-((4-hydroxy-2-methylphenyl) amino)pyrimidin-4-yl)oxy)naphthalen-1-yl)urea;
  1-(3-(tert-butyl)-1-(p-tolyl)-1H-pyrazol-5-yl)-3-(4-((2-((4-hydroxy-3-methoxyphenyl) amino)pyrimidin-4-yl)oxy)naphthalen-1-yl)urea;
  1-(3-(tert-butyl)-1-(p-tolyl)-1H-pyrazol-5-yl)-3-(4-((2-((3-hydroxy-4-methylphenyl) amino)pyrimidin-4-yl)oxy)naphthalen-1-yl)urea;
  1-(3-(tert-butyl)-1-(p-tolyl)-1H-pyrazol-5-yl)-3-(4-((2-((3,4-dimethoxyphenyl)amino) pyrimidin-4-yl)oxy)naphthalen-1-yl)urea;
  1-(3-(tert-butyl)-1-(p-tolyl)-1H-pyrazol-5-yl)-3-(4-((2-((3-chloro-4-methoxyphenyl) amino)pyrimidin-4-yl)oxy)naphthalen-1-yl)urea;

1-(3-(tert-butyl)-1-(p-tolyl)-1H-pyrazol-5-yl)-3-(4-((2-((3-fluoro-4-hydroxyphenyl)amino) pyrimidin-4-yl)oxy)naphthalen-1-yl)urea;

1-(3-(tert-butyl)-1-(p-tolyl)-1H-pyrazol-5-yl)-3-(4-((2-((2-fluoro-4-hydroxyphenyl)amino) pyrimidin-4-yl)oxy)naphthalen-1-yl)urea;

1-(3-(tert-butyl)-1-(p-tolyl)-1H-pyrazol-5-yl)-3-(4-((2-((2-chloro-4-hydroxyphenyl) amino)pyrimidin-4-yl)oxy)naphthalen-1-yl)urea;

1-(3-(tert-butyl)-1-(p-tolyl)-1H-pyrazol-5-yl)-3-(4-((2-((2,4-dihydroxyphenyl)amino) pyrimidin-4-yl)oxy)naphthalen-1-yl)urea; and 1-(3-(tert-butyl)-1-(4-methoxyphenyl)-1H-pyrazol-5-yl)-3-(4-((2-((4-hydroxyphenyl) amino)pyrimidin-4-yl)oxy)naphthalen-1-yl)urea;

and pharmaceutically acceptable salts of any one thereof, including all and stereoisomers and tautomers thereof.

9. A pharmaceutical composition comprising a compound according to claim 1, in combination with one or more pharmaceutically acceptable diluents or carriers.

10. A method of treating chronic respiratory disease in a subject comprising administering to said subject an effective amount of the composition according to claim 9.

11. A method of treating a condition selected from the group consisting of COPD, asthma, cystic fibrosis, sarcoidosis, idiopathic pulmonary fibrosis, allergic rhinitis, rhinitis, sinusitis, conjunctivitis, dermatitis, psoriasis, ulcerative colitis, inflamed joints, rheumatoid arthritis, pancreatitis, cachexia, growth and metastasis of tumours comprising administering to said subject an effective amount of the composition of claim 9.

12. The composition according to claim 9, wherein the composition further comprises at least one anti-viral therapeutic agent selected from the group consisting of zanamivir and oseltamivir.

13. A method of treating a respiratory viral infection in a subject with a chronic condition selected from the group consisting of congestive heart failure, diabetes, cancer, and immunosuppression comprising administering to the subject an effective amount of a pharmaceutical composition according to claim 9.

14. A method of treatment of a condition of a subject selected from the group consisting of COPD, asthma, cystic fibrosis, sarcoidosis, idiopathic pulmonary fibrosis, rhinitis, sinusitis, conjunctivitis, dermatitis, psoriasis, ulcerative colitis, rheumatoid arthritis or osteoarthritis, pancreatitis, cachexia, growth and metastasis of tumours comprising administering to the subject an effective amount of a pharmaceutical composition according to claim 9.

* * * * *